(12) United States Patent
Kim et al.

(10) Patent No.: US 9,783,735 B2
(45) Date of Patent: Oct. 10, 2017

(54) LIQUID CRYSTAL DISPLAY DEVICE AND LIQUID CRYSTAL COMPOSITION USED THEREFOR

(71) Applicants: Samsung Display Co., Ltd., Yongin-si, Gyeonggi-do (KR); DONGJIN SEMICHEM CO., LTD., Incheon (KR)

(72) Inventors: Si Heun Kim, Yongin-si (KR); Beom Soo Shin, Yongin-si (KR); Keun Chan Oh, Yongin-si (KR); Bong Hee Kim, Hwaseong-si (KR); Young Ho Seo, Hwaseong-si (KR)

(73) Assignees: SAMSUNG DISPLAY CO., LTD., Gyeonggi-Do (KR); DONGJIN SEMICHEM CO., LTD., Incheon (KR)

( * ) Notice: Subject to any disclaimer, the term of this patent is extended or adjusted under 35 U.S.C. 154(b) by 0 days.

(21) Appl. No.: 15/059,871

(22) Filed: Mar. 3, 2016

(65) Prior Publication Data
US 2016/0304783 A1  Oct. 20, 2016

(30) Foreign Application Priority Data

Apr. 15, 2015 (KR) .......... 10-2015-0053223
Dec. 21, 2015 (KR) .......... 10-2015-0182962

(51) Int. Cl.
*C09K 19/44* (2006.01)
*C09K 19/34* (2006.01)
(Continued)

(52) U.S. Cl.
CPC .......... *C09K 19/3402* (2013.01); *C07C 43/29* (2013.01); *C07D 309/06* (2013.01);
(Continued)

(58) Field of Classification Search
CPC ..................................... C09K 19/44
See application file for complete search history.

(56) References Cited

U.S. PATENT DOCUMENTS 5,858,270 A  1/1999 Matsui et al.
6,677,003 B2  1/2004 Lussem et al.
(Continued)

FOREIGN PATENT DOCUMENTS

CN  104449761 A  *  3/2015  .......... C07C 43/225
CN  104479688 A     4/2015
(Continued)

OTHER PUBLICATIONS

Extended European Search Report issued from the European Patent Office on Nov. 18, 2016, with respect to European Patent Application No. 16164140.2, filed on Apr. 7, 2016.
(Continued)

*Primary Examiner* — Chanceity Robinson
(74) *Attorney, Agent, or Firm* — Cantor Colburn LLP

(57) ABSTRACT

A liquid crystal display device comprises a first substrate, a second substrate which faces the first substrate, an electrode part which is provided on at least one of the first substrate and the second substrate, and a liquid crystal layer which comprises a liquid crystal composition and is provided between the first substrate and the second substrate. The liquid crystal composition includes a liquid crystal compound of Formula 1.
(Continued)

(56) References Cited

U.S. PATENT DOCUMENTS

| | | | |
|---|---|---|---|
| 6,908,645 | B2 | 6/2005 | Kirsch et al. |
| 7,651,742 | B2 | 1/2010 | Wittek et al. |
| 2003/0052306 | A1 | 3/2003 | Ichinose et al. |

FOREIGN PATENT DOCUMENTS

| | | | | |
|---|---|---|---|---|
| CN | 104498053 A | 4/2015 | | |
| CN | 104610983 A | 5/2015 | | |
| CN | 104673323 A | 6/2015 | | |
| CN | WO 2016078389 A1 | * | 5/2016 | ........... C07C 43/225 |
| EP | 1199346 | 9/2001 | | |
| JP | 9176645 A | 7/1997 | | |
| JP | 2004149774 | 5/2004 | | |
| WO | 9611897 | 4/1996 | | |
| WO | 9724411 | 7/1997 | | |

OTHER PUBLICATIONS

Henok H. Kinfe, et al., "Solvent-Free NaHSO4—Si02-Catalyzed Efficient Tetrahydropyranylation of Alcohols and Phenols", Synthetic Communications, 43:9, pp. 1237-1242, 2013.

Manfred Schlosser, "The 2×3 Toolbox of Organometallic Methods for Regiochemically Exhaustive Functionalization", Angew. Chem. Int. Ed. 2005, v. 44, pp. 376-393.

Manfred Schlosser, "The Organometallic Approach to Molecular Diversity—Halogens as Helpers", Eur. J. Org. Chem. 2001, pp. 3975-3984.

Takashi Hiraoka, et al., "Novel Liquid Crystalline Four Ring Chain Difluoromethyleneoxy Compounds for Quicker Response LC Mixtures", Mol. Cryst. Liq. Cryst., 509:1, pp. 89/831-95/837, 2009.

\* cited by examiner

Formula 1 wherein $R_1$, $R_2$, $A_{11}$, $A_{12}$, $A_{13}$, $A_{21}$, $A_{22}$, $Z_{11}$, $Z_{12}$, $Z_{13}$, $Z_{21}$, $Z_{22}$, a, b, c, d, and e are as described herein.

19 Claims, 1 Drawing Sheet

(51) Int. Cl.

| | |
|---|---|
| *C09K 19/04* | (2006.01) |
| *C09K 19/20* | (2006.01) |
| *C09K 19/30* | (2006.01) |
| *C07C 43/29* | (2006.01) |
| *C07D 309/06* | (2006.01) |
| *C07D 319/06* | (2006.01) |
| *C09K 19/54* | (2006.01) |
| *C09K 19/12* | (2006.01) |

(52) U.S. Cl.
CPC ........ *C07D 319/06* (2013.01); *C09K 19/0403* (2013.01); *C09K 19/20* (2013.01); *C09K 19/3066* (2013.01); *C09K 19/54* (2013.01); *C09K 2019/0466* (2013.01); *C09K 2019/123* (2013.01); *C09K 2019/301* (2013.01); *C09K 2019/3004* (2013.01); *C09K 2019/3016* (2013.01); *C09K 2019/3019* (2013.01); *C09K 2019/3422* (2013.01)

LIQUID CRYSTAL DISPLAY DEVICE AND LIQUID CRYSTAL COMPOSITION USED THEREFOR

CROSS-REFERENCE TO RELATED APPLICATION

This application claims priority to Korean Patent Application No. 10-2015-0053223, filed on Apr. 15, 2015, and 10-2015-0182962, filed on Dec. 21, 2015, in the Korean Intellectual Property Office, and all the benefits accruing therefrom under 35 U.S.C. §119, the disclosure of which is incorporated herein by reference in its entirety.

BACKGROUND

1. Technical Field

This disclosure relates to a liquid crystal display (LCD) device and a liquid crystal composition used therefor.

2. Description of the Related Art

A liquid crystal display device may include a first substrate having a plurality of pixels, a second substrate, and a liquid crystal layer which is interposed between the first and second substrates. The liquid crystal display device changes a transmittance ratio of light in the liquid crystal layer according to an electric field generated between each of the pixel electrodes and a common electrode, thereby displaying an image. The liquid crystal display device may include a plurality of pixels each of which may include a pixel electrode.

Recently, investigations have been made to display not only a 2D image but a 3D image by using the liquid crystal display device, and there has been a need for a solution which provides more image information to a user. Therefore, there is a need for a liquid crystal display device which has a high driving speed as well as higher reliability, when compared with conventional liquid crystal display devices.

As disclosed herein, an exemplary embodiment provides a single liquid crystal compound with high dielectric anisotropy and high refractive index anisotropy as well as improved low temperature stability, and a liquid crystal composition comprising the same.

Another exemplary embodiment provides a liquid crystal display device comprising the liquid crystal composition with high dielectric anisotropy and high refractive index anisotropy as well as improved low temperature stability.

According to an embodiment a liquid crystal display device comprises a first substrate, a second substrate which faces the first substrate, an electrode part which is provided on at least one of the first substrate and the second substrate, and a liquid crystal layer which comprises a liquid crystal composition and is provided between the first substrate and the second substrate.

According to an embodiment, the liquid crystal composition comprises at least one liquid crystal compound represented as Formula 1.

In Formula 1, $R_1$ represents hydrogen or an alkyl having 1-15 carbon atoms, in which at least one —$CH_2$— group may be independently replaced by —C≡C—, —$CF_2$O—, —CH=CH—, —O—, —CO—O—, —O—CO— or —O—CO—O— in such a way that no oxygen atoms bind to each other, and 1-3 hydrogen atoms may be replaced by halogen atoms, $R_2$ represents —F, —Cl, —$CF_3$, —$CHF_2$, —$CH_2F$, —$OCF_3$, —CN, —NCS, or an alkyl having 1-5 carbon atoms substituted with one to three of —F, and —$CH_2$— groups are optionally replaced by O atoms independently of each other, in such a way that no two oxygen atoms bind each other, (F) represents that a hydrogen atom is optionally replaced by —F, $A_{11}$, $A_{12}$, $A_{13}$, $A_{21}$ and $A_{22}$ represent one of the following structures independently of each other:

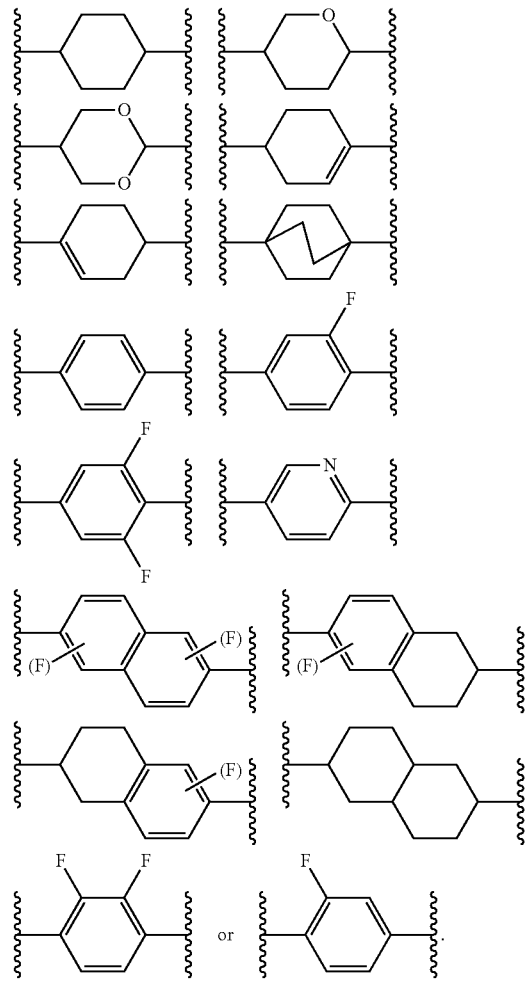

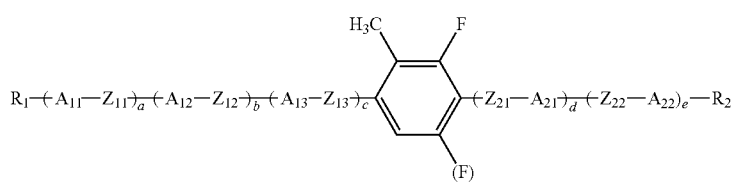

Formula 1

$Z_{11}$, $Z_{12}$, $Z_{13}$, $Z_{21}$ and $Z_{22}$, may be each independently a single bond, —CH$_2$CH$_2$—, —CH=CH—, —CH$_2$O—, —OCH$_2$—, —C≡C—, —CH$_2$CF$_2$—, —CHFCHF—, —CF$_2$CH$_2$—, —CH$_2$CHF—, —CHFCH$_2$—, —C$_2$F$_4$—, —COO—, —OCO—, —CF$_2$O—, or —OCF$_2$— independently of each other, a, b, c, d and e are each independently an integer from 0 to 3, and a+b+c+d+e is less than or equal to 5.

According to an embodiment, at least one of $Z_{11}$, $Z_{12}$, $Z_{13}$, $Z_{21}$ and $Z_{22}$ may be —CF$_2$O—.

According to an embodiment, d and e are 0, and R$_2$ may be —F, —OCF$_3$ or —CF$_3$.

According to an embodiment, $Z_{13}$ is —CF$_2$O—, d and e are 0, and R$_2$ is —F, —OCF$_3$, or —CF$_3$.

According to an embodiment, the liquid crystal compound of Formula 1 may be represented as Formula 1-1.

Formula 1-1

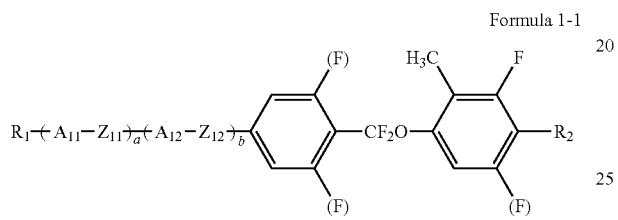

$R_1$, $R_2$, $A_{11}$, $A_{12}$, $Z_{11}$, $Z_{12}$, a, and b are the same as in the definitions for Formula 1.

According to an embodiment, the liquid crystal compound of Formula 1-1 may be represented as Formula 1-2.

Formula 1-2

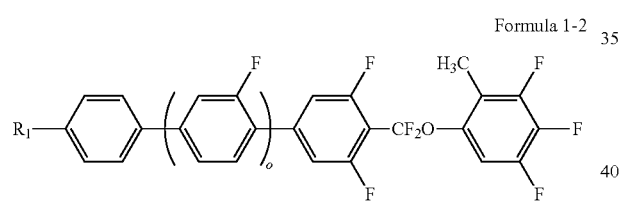

$R_1$ is the same as in the definition for Formula 1, and o is 0 or 1.

According to an embodiment, the liquid crystal composition may further comprise at least one liquid crystal compound represented as Formula 2.

Formula 2

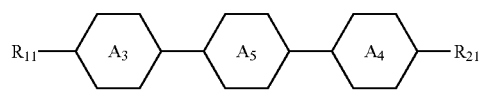

$R_{11}$ is the same as in the definition for $R_1$ in Formula 1, $R_{21}$, in addition to the definition of $R_1$ of Formula 1, represents —F, —Cl, —CF$_3$, or —OCF$_3$, $A_3$ and $A_4$ are 1,4-cyclohexylene or 1,4-phenylene, independently of each other, and $A_5$ represents one of the following structures:

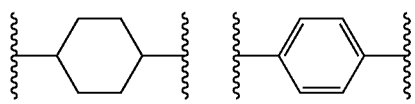

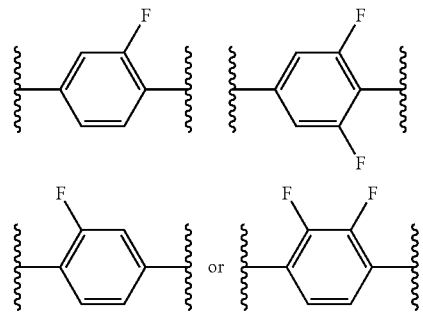

According to an embodiment, the liquid crystal composition further comprises a liquid crystal compound which is represented as Formula 3.

Formula 3

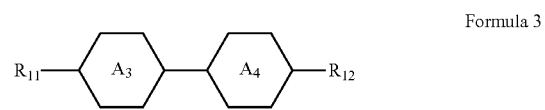

$R_{11}$ and $R_{12}$ are independently the same as in the definition of $R_1$ in Formula 1, and $A_3$ and $A_4$ are independently 1,4-cyclohexylene or 1,4-phenylene.

According to an embodiment, the liquid crystal composition may further comprise a liquid crystal compound which is represented as Formula 4.

Formula 4

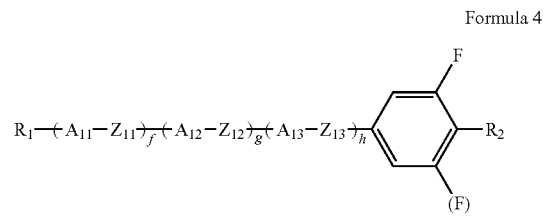

In Formula 4, $R_1$ and $R_2$ are the same as in the definitions of $R_1$ and $R_2$ in Formula 1, $A_{11}$, $A_{12}$, $A_{13}$, $Z_{11}$, $Z_{12}$ and $Z_{13}$ are also the same as in the definitions of $A_{11}$, $A_{12}$, $A_{13}$, $Z_{11}$, $Z_{12}$ and $Z_{13}$ in Formula 1, f, g, and h are each independently 0 or 1, and f+g+h is 2 or 3.

According to an embodiment, the liquid crystal composition may further comprise at least one liquid crystal compound which is represented as any one of Formulae 5-7.

Formula 5

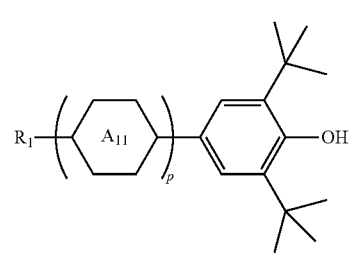

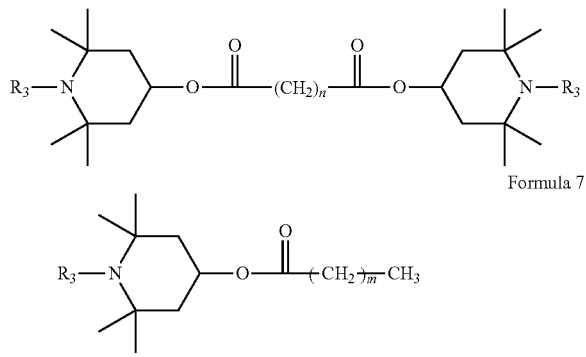

Formula 6

Formula 7

R$_1$ and A$_{11}$ are the same as in the definitions for Formula 1, p is 0 or 1, R$_3$ represents hydrogen, oxygen radical, or an alkyl having 1-15 carbon atoms, in which at least one —CH$_2$— group may be independently replaced by —C≡C—, —CF$_2$O—, —CH=CH—, —O—, —CO—O—, —O—CO— or —O—CO—O— in such a way that no two oxygen atoms bind to each other, one to three hydrogen atoms may be replaced by halogen atoms, n is 1-12, and m is 0-12.

According to an embodiment, the liquid crystal composition further comprises a pitch modifying agent which is represented as Formula 8.

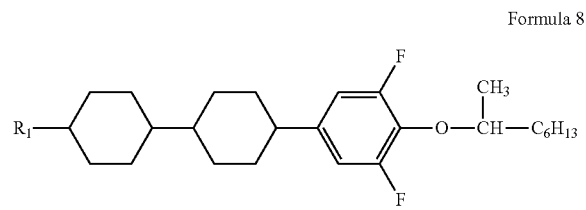

Formula 8

R$_1$ is the same in the definition for Formula 1.

By preparing the liquid crystal composition according to the present disclosure, a liquid crystal composition which has improved low temperature stability as well as a high dielectric constant and a high refractive index, may be manufactured.

Also, by preparing the liquid crystal composition according to the present disclosure, it is possible to provide a liquid crystal composition which is optimized for various modes of liquid crystal display devices such as e.g., twisted nematic (TN), super twisted nematic (STN), in plane switching (IPS), fringe field switching (FFS) or plane to line switching (PLS), etc.

BRIEF DESCRIPTION OF THE DRAWINGS

The above and other advantages and features of this disclosure will become more apparent by describing in further detail exemplary embodiments thereof with reference to the accompanying drawings, in which.

DETAILED DESCRIPTION

Figure 1:
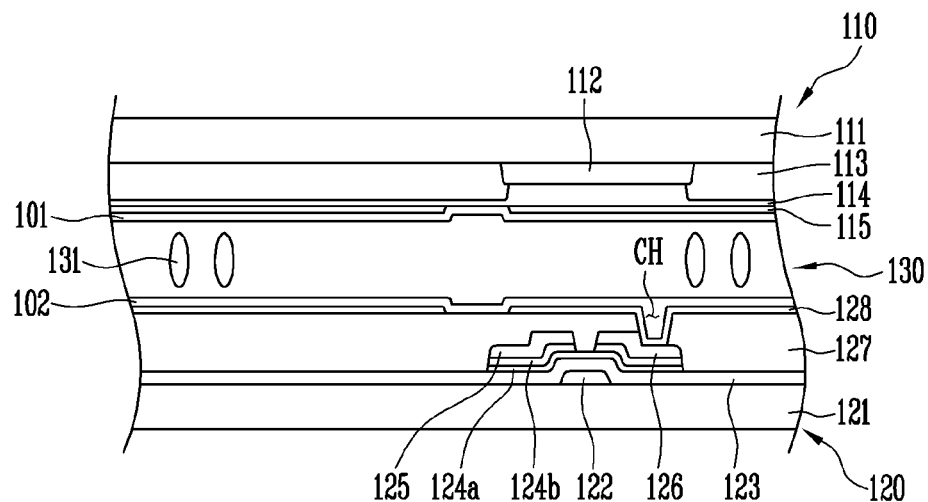
FIG. 1 is a diagram illustrating a liquid crystal display device according to one embodiment.

The present disclosure may be embodied with various variations and in various shapes, and, therefore, specific embodiments will be illustrated in figures and described in detail in this section. On the other hand, the figures are not intended to limit the present disclosure to the disclosed embodiment, and they are to be construed to include all variations, equivalents, and replacements which fall into the spirit and the technical scope of the present disclosure. In the drawings, sizes of layers and regions may be exaggerated for clarity.

Although the terms "first", "second", etc. may be used herein to describe various elements, these elements should not be limited by these terms. These terms may be used to distinguish one element from another element. Thus, a first element described in this application may be termed a second element without departing from teachings of one or more embodiments. The description of an element as a "first" element may not require or imply the presence of a second element or other elements. The terms "first", "second", etc. may also be used to differentiate different categories or sets of elements. For conciseness, the terms "first", "second", etc. may represent, for example, "first-category (or first-set)", "second-category (or second-set)", etc., respectively.

When a first element is referred to as being "on", "connected to", or "coupled to" a second element, the first element may be directly on, directly connected to, or directly coupled to the second element, or one or more intervening elements may be present. In contrast, when a first element is referred to as being "directly on", "directly connected to", or "directly coupled to" a second element, there are no intervening elements intentionally provided between the first element and the second element. When an element A is "between" two other elements B and C, Element A may be directly on element B and directly on element C, or there may be other intervening layers between A and B, between A and C, or between both A and B and A and C. Like numbers may refer to like elements in this application. The term "and/or" includes any and all combinations of one or more of the associated items. "Or" means "and/or."

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments are described herein with reference to cross-section illustrations that are schematic illustrations of embodiments (and intermediate structures). As such, variations from the shapes of the illustrations as a result, for example, of manufacturing techniques and/or tolerances, are to be expected. Thus, embodiments should not be construed as limited to the particular shapes of regions illustrated herein but are to include deviations in shapes that result, for example, from manufacturing. For example, an implanted region illustrated as a rectangle may have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of embodiments.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" may mean within one or more standard deviations, or within ±30%, 20%, 10% or 5% of the stated value.

As used herein, "alkyl" means a straight or branched chain, saturated, monovalent hydrocarbon group (e.g., methyl or hexyl) having the specified number of carbon atoms.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following, preferred embodiments will be explained in more detail.

The present disclosure relates to a liquid crystal compound as a material for a liquid crystal display device, and a composition including the liquid crystal compound.

Single liquid crystal compounds which constitute a liquid crystal product may be an organic matter with a molecular weight of about 200-600 g/mol and have a molecular structure of a long bar. Molecular structures of liquid crystal are classified into a core group which maintains a straight feature, a terminal group which has flexibility, and a linkage group for a specific use. Without being bound by theory, the terminal group has, at one or both sides, a chain formation which is easily bendable (alkyl, alkoxy, alkenyl etc.) for maintaining flexibility, and introduces, at the other side, a polar group (—F, —CN, —OCF$_3$ etc.) for modifying a physical property of the liquid crystal such as a dielectric constant.

According to the property and an application mode of a liquid crystal display (LCD) panel, the LCD may have various kinds of modes such as twist nematic (TN), super-twisted nematic (STN), in-plane switching (IPS), fringe field switching (FFS) etc. In these various liquid crystal display devices, it is difficult to meet product requirements such as a temperature of a clearing temperature, dielectric anisotropy, refractive index anisotropy, rotational viscosity etc. by using one or two liquid crystal compounds, and, therefore, 7-20 kinds of single liquid crystal compounds may be mixed to manufacture the liquid crystal compound.

Some main elements of general properties required for this liquid crystal compound are as listed in table 1.

TABLE 1

| Required physical properties of liquid crystal composition | Reference value | Related properties of LCD |
|---|---|---|
| low temperature stability | no higher than −20° C. | operation temperature |
| clearing temperature (Tc) | no lower than 70° C. | operation temperature |
| dielectric anisotropy (Δε) | no smaller than 2 | threshold voltage, response time |
| refractive index anisotropy (Δn) | no smaller than 0.07 | brightness, cell gap |
| rotational viscosity (γ1) | as small as possible | response time |
| elastic modulus ($K_{11}$, $K_{22}$, $K_{33}$ average value) | 8-18 pN | response time, threshold voltage, brightness |

As shown in table 1, irrespective of an application mode of the LCD panel, low rotational viscosity is preferred, and the refractive index anisotropy is preferably greater than or equal to 0.07 although an optimum value therefor is varied according to the cell gap of the LCD. Also, as for an active matrix-LCD (AM-LCD), it requires a specific resistance which is greater than or equal to $10^{13}$ Ωm. There is a need for manufacturing a mixture which satisfies these properties and enables the LCD panel to operate even at a low temperature lower than or equal to −25° C.

When not fewer than 10 kinds of single liquid crystal compounds are mixed, although most eutectic points are not higher than −20° C., recrystallization may happen due to a single liquid crystal compound with a high melting point, when the mixture is left at a low temperature for a long time. Thus, in order to avoid this recrystallization, alkyl homologues with different alkyl derivatives are adequately mixed. On the other hand, single liquid crystal compounds tend to have long alkyl groups for enhancing refractive index anisotropy or dielectric anisotropy, and these long alkyl groups may increase a rotational viscosity while decreasing an elastic modulus. This increase of the rotational viscosity and the decrease of the elastic modulus may increase a response time.

For example, as shown in table 2, compound no. 2 having two more methylene units (methylene, —CH$_2$—) than compound no. 1 has a low melting point, which makes it preferable for low temperature stability; however, its rotational viscosity (γ1) increases by 20 mPas or more, which increases the response time of the LCD panel (Hiraoka, H, (2009), *Mol. Cryst. Liq. Cryst.*, Vol 509, pp 89).

TABLE 2

| no. | structure | melting point | Tc | ΔE | Δn | γ1 |
|---|---|---|---|---|---|---|
| 1 | (C₃H₇-phenyl-difluorophenyl-difluorophenyl-CF₂O-difluorophenyl-F) | 86° C. | 96° C. | 34 | 0.210 | 387 |
| 2 | (C₅H₁₁-phenyl-difluorophenyl-difluorophenyl-CF₂O-difluorophenyl-F) | 64° C. | 96° C. | 32 | 0.197 | 411 |

Therefore, a single liquid crystal compound with high dielectric anisotropy, high refractive index anisotropy, low viscosity, and a low melting point is desired, and the present disclosure provides a single liquid crystal compound with high dielectric anisotropy and high refractive index anisotropy as well as low viscosity and a low melting point.

The liquid crystal compound according to an embodiment is represented as Formula 1.

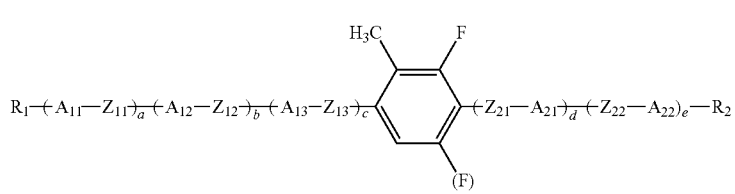

Formula 1

In Formula 1, $R_1$ represents hydrogen or an alkyl having 1-15 carbon atoms, in which at least one —CH₂— group may be independently replaced by —C≡C—, —CF₂O—, —CH=CH—, —O—, —CO—O—, —O—CO— or —O—CO—O— in such a way that no two oxygen atoms bind to each other, and 1-3 hydrogen atoms may be replaced by halogen atoms.

Also, as for $R_1$, when at least one —CH₂— group is replaced by a double bond, the double bond may be introduced into a terminal of an even-numbered carbon when the number of carbon atoms of $R_1$ is even. For example, when a double bond is introduced into $R_1$, it may be CH₂=CH—, or CH₂=CH—CH₂—CH₂—. When the number of carbon atoms of $R_1$ is an odd number greater than or equal to 3, the double bond may be introduced between an even-numbered carbon and an odd-numbered carbon next thereto, when counted from the terminal. For example, when a double bond is introduced into $R_1$, it may be CH₃—CH=CH—, or CH₃—CH=CH—CH₂—CH₂—. Without being bound by theory, by introducing double bonds to $R_1$, it is possible to decrease the rotational viscosity, increase the clearing temperature, and control the elastic modulus.

In Formula 1, $R_2$ may be a polar group, —F, —Cl, —CF₃, —CHF₂, —CH₂F, —OCF₃, —CN, —NCS, or an alkyl substituted with one to three of —F, in which —CH₂— groups may be replaced with an O atom independently of each other, in such a way that no two oxygen atoms bind each other. According to an embodiment, $R_2$ may be —F, —Cl, —CF₃, or —OCF₃.

In Formula 1, (F) represents that substituted hydrogen atom is optionally replaced by F, and $A_{11}$, $A_{12}$, $A_{13}$, $A_{21}$ and $A_{22}$ represent the following structures independently of each other:

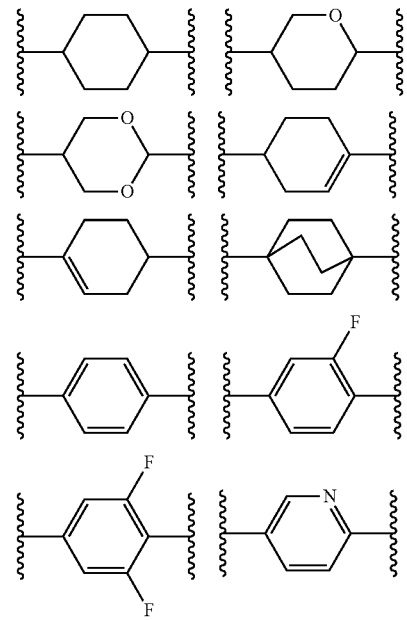

behaves substantially the same as the ring substituted with a methyl group. On the other hand, since the positive dielectric anisotropy is decreased due to fluorine, it is hard to obtain a desired amount of large dielectric anisotropy. In order to increase the positive dielectric anisotropy, fluorine groups may be introduced into the rings at second and sixth locations.

The liquid crystal compound of Formula 1 may include a compound having a structure represented a Formula 1A, and, in Formula 1A, $R_1$ may be the same as in Formula 1.

Formula 1A

[1]
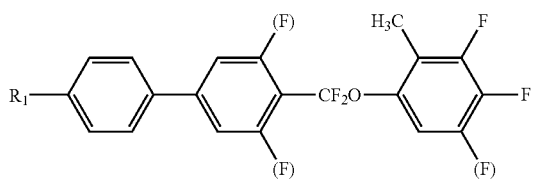

[2]
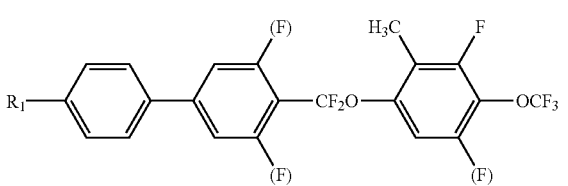

[3]
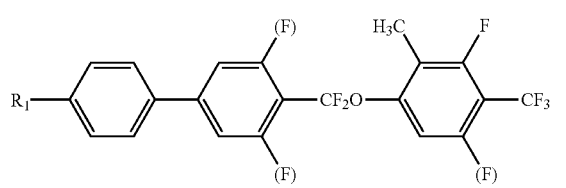

[4]
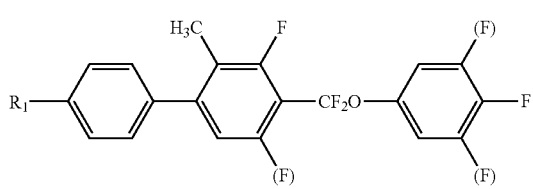

[5]
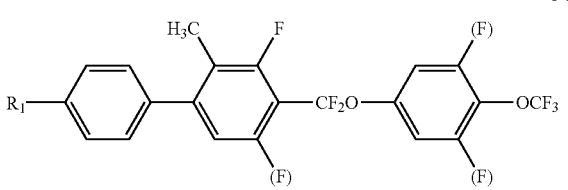

[6]
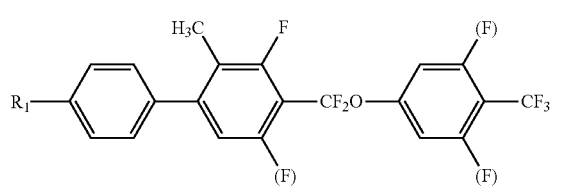

According to an embodiment and without being bound by theory, 1,4-phenylene may be used as $A_{11}$, $A_{12}$, $A_{13}$, $A_{21}$, and $A_{22}$ for high refractive index anisotropy, and a ring structure including fluorine or oxygen may be used to improve dielectric anisotropy.

$Z_{11}$, $Z_{12}$, $Z_{13}$, $Z_{21}$ and $Z_{22}$, are each independently a single bond, —CH$_2$CH$_2$—, —CH=CH—, —CH$_2$O—, —OCH$_2$—, —C≡C—, —CH$_2$CF$_2$—, —CHFCHF—, —CF$_2$CH$_2$—, —CH$_2$CHF—, —CHFCH$_2$—, —C$_2$F$_4$—, —COO—, —OCO—, —CF$_2$O—, or —OCF$_2$—.

$Z_{11}$, $Z_{12}$, $Z_{13}$, $Z_{21}$, and $Z_{22}$ may be selectively combined in consideration of dielectric anisotropy, rotational viscosity, refractive index anisotropy etc. According to an embodiment, at least one of $Z_{11}$, $Z_{12}$, $Z_{13}$, $Z_{21}$ and $Z_{22}$ may be —CF$_2$O—. When at least one of $Z_{11}$, $Z_{12}$, $Z_{13}$, $Z_{21}$, and $Z_{22}$ is —CF$_2$O—, the liquid crystal compound may have high dielectric anisotropy. In particular, when $Z_{13}$ is —CF$_2$O—, the dielectric anisotropy may be improved while minimizing a decrease in a clearing temperature of the liquid crystal compound. According to an embodiment, $Z_{11}$, $Z_{12}$, $Z_{13}$, $Z_{21}$, and $Z_{22}$, respectively, may be a single bond, and, in this case, the compound may have low rotational viscosity.

Further, a, b, c, d and e, respectively, independently represent a value 0-3, and a+b+c+d+e is less than or equal to 5.

The liquid crystal compound of Formula 1 may have a higher dielectric constant than other kinds of liquid crystal, and its rotational viscosity may be relatively low in consideration of the high dielectric constant. Also, the liquid crystal compound of Formula 1 may have a relatively lower melting point with respect to a molecular weight than other kinds of liquid crystal compounds.

In an embodiment, when there is a ring substituted by methyl group between rings, the methyl substituted ring increases an angle between the rings. Without being bound by theory, when the angle between rings increases due to the methyl substituted ring, packing density between liquid crystal molecules is decreased, and the melting point is lowered. In Formula 1, a third location in 1,4-phenylene is substituted with a methyl group, and, therefore, the packing density of the liquid crystal compound of Formula 1 is decreased and the melting point is lowered as well. Without being bound by theory, when there are two or more alkyl groups with 2 carbon atoms present between the rings, a ratio between a major axis and a minor axis of the liquid crystal molecule is decreased, and the clearing temperature is dramatically lowered as well. Also, when there is a ring substituted with fluorine present between the rings, the ring

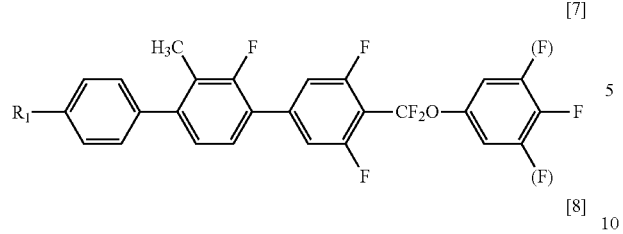
[7]
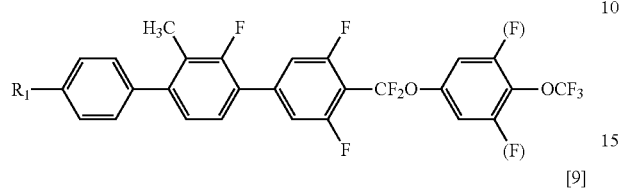
[8]
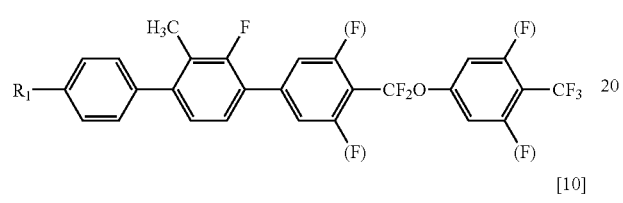
[9]
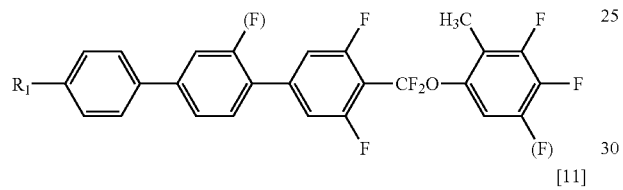
[10]
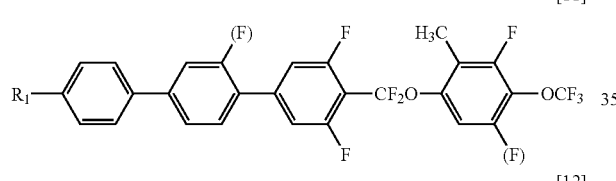
[11]
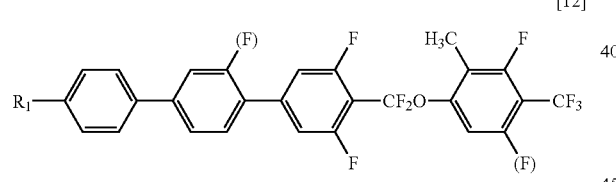
[12]
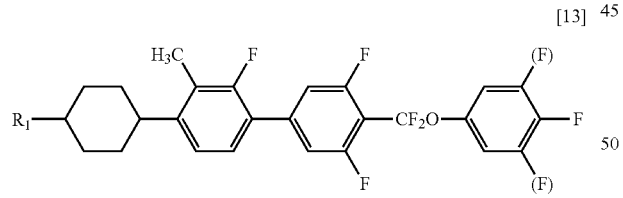
[13]
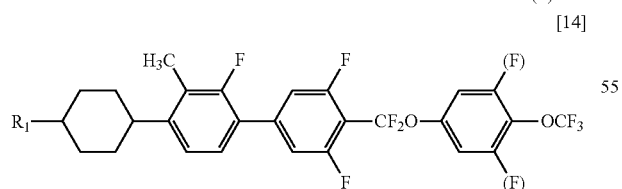
[14]
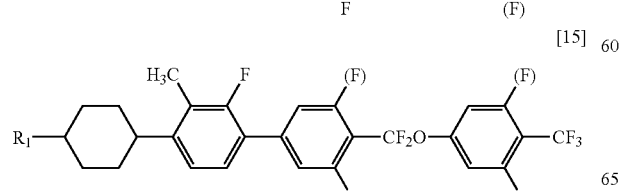
[15]
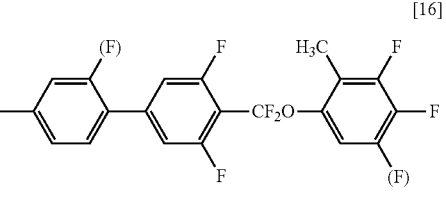
[16]
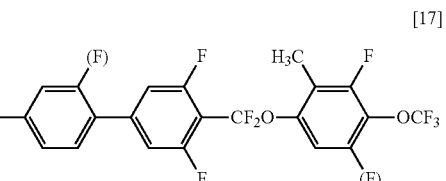
[17]
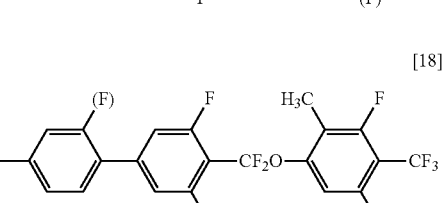
[18]
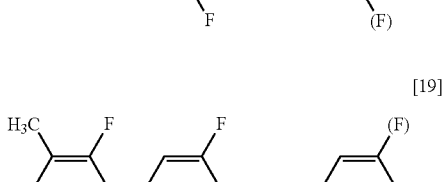
[19]
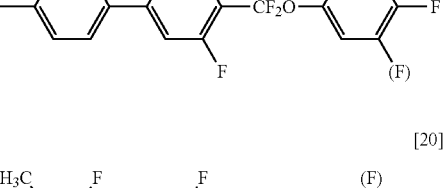
[20]
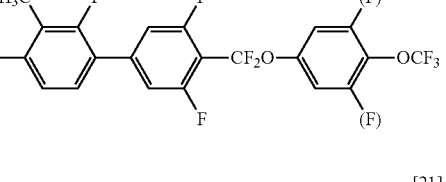
[21]
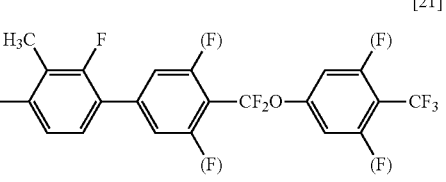
[22]
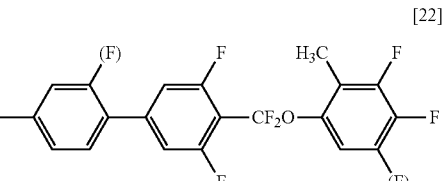
[23]
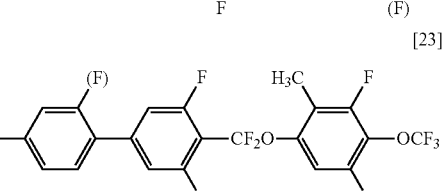

-continued

[24]
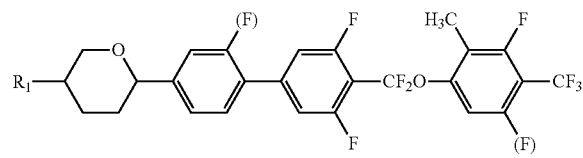

[25]
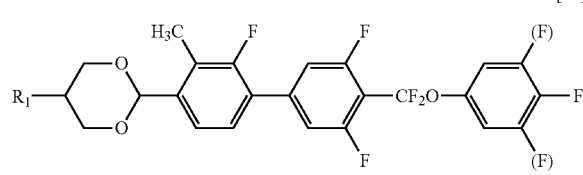

[26]
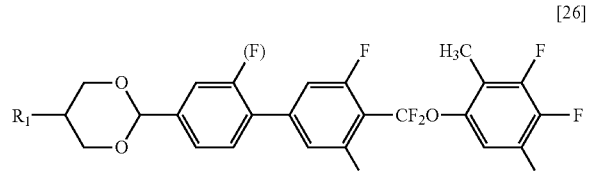

[27]
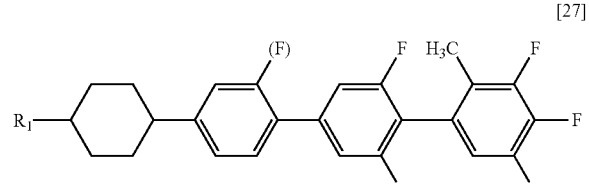

[28]
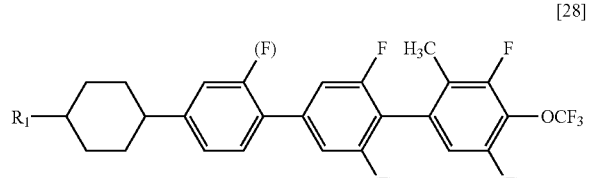

[29]
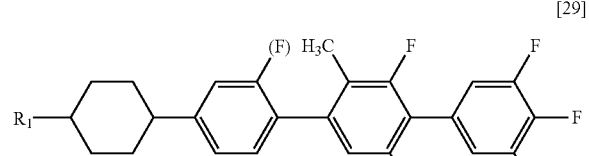

[30]
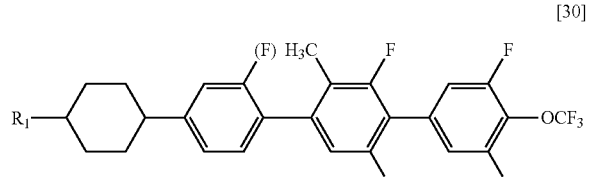

[31]
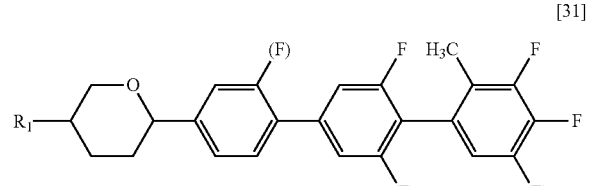

-continued

[32]
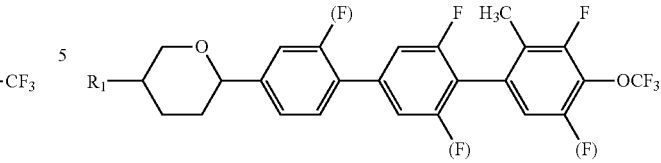

[33]
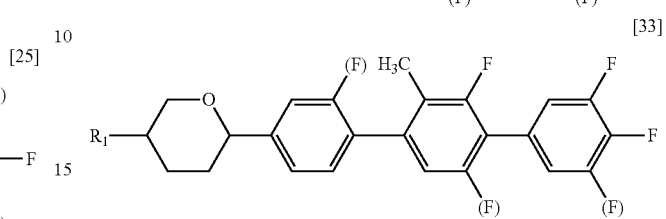

[34]
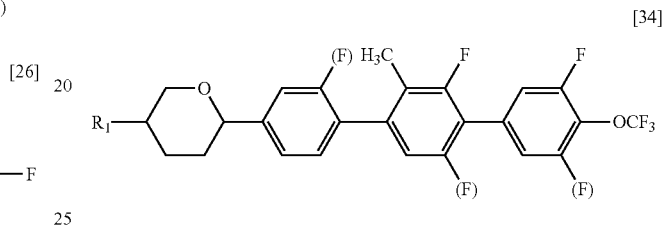

For example, in some embodiments, the liquid crystal compound may be the liquid crystal compound represented as Formula 1 in which at least one of $Z_{11}$, $Z_{12}$, $Z_{13}$, $Z_{21}$ and $Z_{22}$ is —$CF_2O$—. According to another embodiment, the liquid crystal compound may be the liquid crystal compound in which d and e are 0, and $R_2$ is —F, —$OCF_3$ or —$CF_3$. According to a still another embodiment, the liquid crystal compound may be the liquid crystal compound in which $Z_{13}$ is $CF_2O$, d and e are 0, and $R_2$ is —F, —$OCF_3$, or —$CF_3$.

More specifically, according to an embodiment, the liquid crystal compound of the Formula 1 may be one of the compounds with the structure represented as Formula 1-1.

Formula 1-1
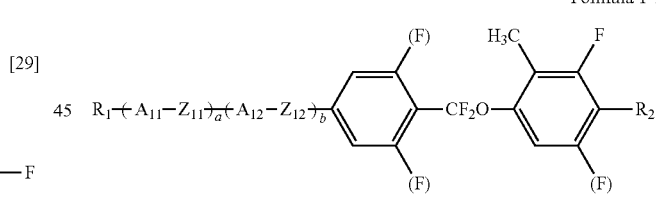

$R_1$, $R_2$, $A_{11}$, $A_{12}$, $Z_{11}$, and $Z_{12}$ are the same as in the definitions for Formula 1.

According to an embodiment, the liquid crystal compound of the Formula 1 may be at least one of the compounds with the structure represented as Formula 1-2.

Formula 1-2
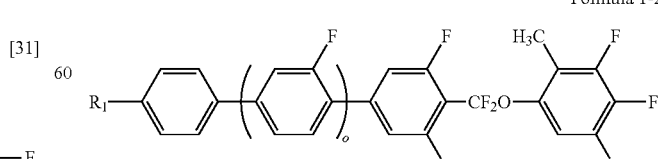

wherein o is 0 or 1.
$R_1$ is the same as in Formula 1.

The liquid crystal compound of Formula 1-2 may be at least one of compounds with the structures represented in Formulae 1-2-1, 1-2-2, and 1-2-3.

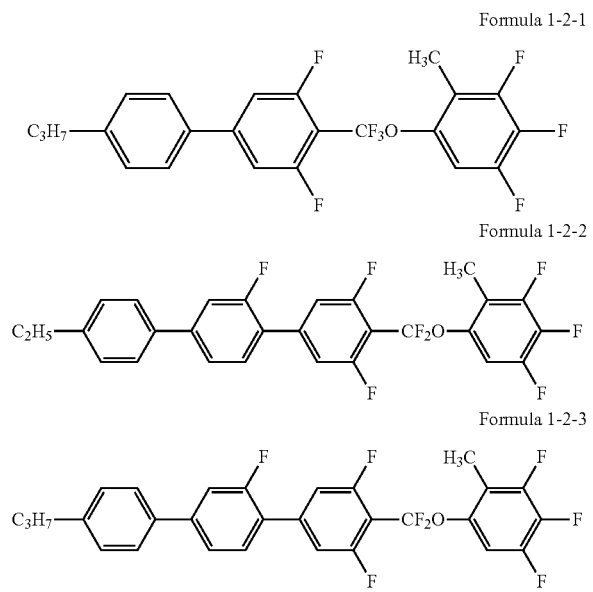

Formula 1-2-1

Formula 1-2-2

Formula 1-2-3

In still another embodiment, the liquid crystal composition comprises or consists of the liquid crystal compound of Formula 1.

As for the liquid crystal composition according to an embodiment, the liquid crystal compound of Formula 1 is included at a concentration of 1% or higher by weight with respect to an overall weight of the liquid crystal composition.

The liquid crystal composition according to an embodiment may include the liquid crystal compound of Formula 1 at a concentration of 1% or higher by weight, or in a range 1-40% by weight, or in a range 1-30% by weight. When the concentration of the liquid crystal compound of Formula 1 is lower than 1% by weight, it is hard to obtain high dielectric constant and guarantee low temperature stability, while when the concentration is higher than 40% by weight, reliability, etc. of the display device is degenerated due to a small direct current (DC) generated in the display device.

The liquid crystal composition according to an embodiment may preferably include one or two or more of the liquid crystal compounds with the structure of Formula 1-2, and, in this case, low temperature stability is maintained for a long time.

In particular, the liquid crystal composition according to an embodiment may include the liquid crystal compound of Formula 1-2-1. As for Formula 1-2-1, it is a material with low rotational viscosity with dielectric anisotropy of 20 and rotational viscosity of 114 mPas. Thus, when the dielectric anisotropy of the liquid crystal composition is about 3-6, it is effective to include the liquid crystal compound of Formula 1-2-1 at the concentration of about 3-7% by weight in order for the low rotational viscosity of the liquid crystal composition. In case of the liquid crystal composition with dielectric anisotropy of 10 or higher, the dielectric anisotropy may be easily modified when about the material of Formula 1-2-2 and/or 1-2-3 with the dielectric anisotropy of a single substance of 30 or higher is included at the concentration of 10% or higher by weight.

According to an embodiment, in addition to the liquid crystal compound of Formula 1, the liquid crystal composition which is mixed with one or more of the following additional liquid crystal compounds may have improved low temperature stability, high dielectric anisotropy, and low rotational viscosity:

In the liquid crystal composition according to an embodiment, the liquid crystal compound may further include at least one compound of the liquid crystal compounds of Formula 2.

Formula 2

$R_{11}$ is the same as in the definition for $R_1$ in Formula 1, $R_{21}$, in addition to the definition of $R_1$ for Formula 1, represents —F, —Cl, —$CF_3$, or —$OCF_3$, $A_3$ and $A_4$ are 1,4-cyclohexylene or 1,4-phenylene, independently of each other, and $A_5$ may have the structure represented as the following structures:

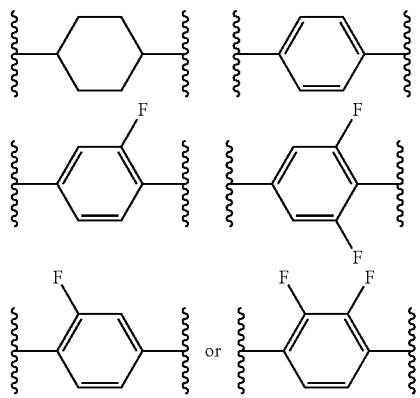

According to an embodiment, the liquid crystal compound of Formula 2 is a compound with the structure represented as Formula 2-1.

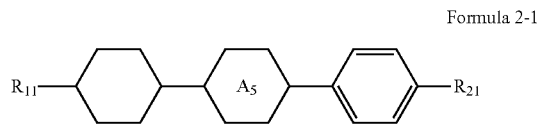

Formula 2-1

$R_{11}$, $R_{21}$ and $A_5$ are the same as in Formula 2.

The liquid crystal compound of Formula 2-1 may be used at a higher temperature than the liquid crystal compound of Formula 1, and it is possible to compensate for high temperature stability and low viscosity when combining the liquid crystal compound of Formula 2-1 with the liquid crystal compound of Formula 1. When the compound of Formula 2-1 is mixed with the compound of Formula 1, it is preferable to use the liquid crystal compound of Formula 2-1 at the concentration of about 5-35% by weight. When the concentration of the liquid crystal compound of Formula 2-1 is not higher than 5% by weight, a clearing temperature rising effect is reduced, while when it is 35% or higher by weight, a smectic phase is developed which reduces the low temperature stability.

The liquid crystal compound of Formula 2-1 may be the compound with the structure represented as Formula 2-1-1a or Formula 2-1-1b.

Formula 2-1-1a

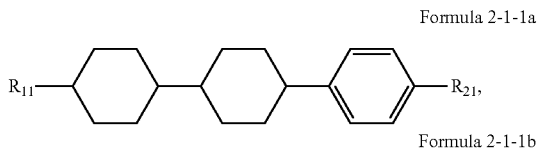

Formula 2-1-1b $R_{11}$ and $R_{21}$ are the same as in Formula 2.

The liquid crystal compound of Formula 2-1-1a or Formula 2-1-1b may be at least one of the compounds with the structures represented as Formula 2-1-1-1 and/or Formula 2-1-1-2.

Formula 2-1-1-1

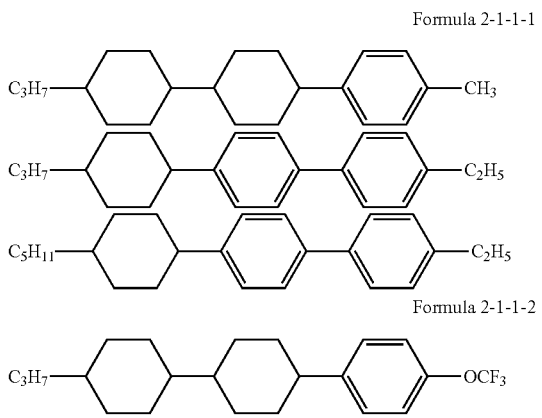

Formula 2-1-1-2

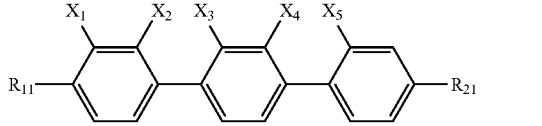

According to an embodiment, the liquid crystal compound of the Formula 2 may be a compound with the structure represented as Formula 2-2.

Formula 2-2

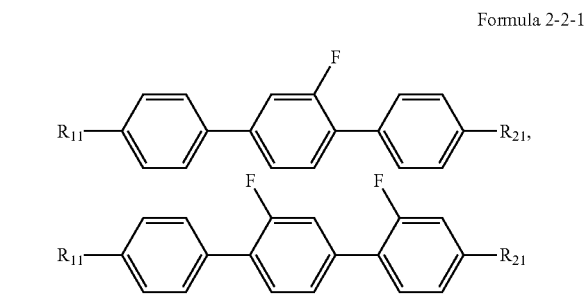

$R_{11}$ and $R_{21}$ are the same as in the definitions for Formula 2, $X_1$ to $X_5$, are independently —H or —F, and at least one of $X_3$ or $X_4$ is —F.

The liquid crystal compound of Formula 2-2 has higher refractive index anisotropy and a higher clearing temperature than the liquid crystal compound of Formula 1. Thus, the liquid crystal compound of Formula 2-2 may compensate for the refractive index anisotropy and the low clearing temperature of the liquid crystal composition when combined with the liquid crystal compound of Formula 1. When mixing the compounds of Formula 1 and Formula 2-2, the liquid crystal compound of Formula 2-2 may be included at the concentration of 1-20% by weight with respect to the overall composition. When the liquid crystal compound of Formula 2-2 is included at the concentration of higher than 20% by weight, the refractive index anisotropy may become too high to be used for the liquid crystal display device. Also, when it is used at the concentration of 1% or lower by weight, the refractive index anisotropy may be difficult to control in the composition.

The liquid crystal compound of Formula 2-2 may be at least one of the liquid crystal compounds with the structure of Formula 2-2-1.

Formula 2-2-1

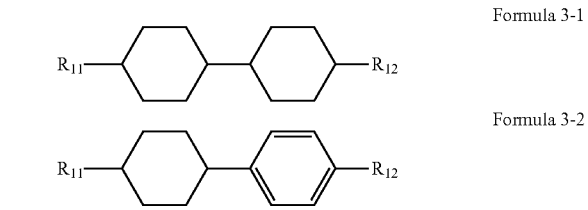

$R_{11}$ and $R_{21}$ are the same as in Formula 2.

In the liquid crystal composition according to an embodiment, the liquid crystal compound may further include at least one compound of the liquid crystal compounds of Formula 3.

Formula 3

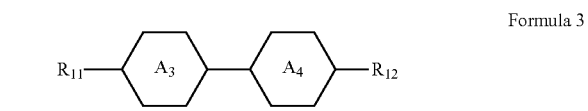

$R_{11}$ and $R_{12}$ are independently the same as in the definition of $R_1$ in Formula 1, and $A_3$ and $A_4$ are independently 1,4-cyclohexylene or 1,4-phenylene. According to an embodiment, the liquid crystal compound of Formula 3 is the compound with the structure represented as Formulae 3-1 or 3-2.

Formula 3-1

Formula 3-2

$R_{11}$ and $R_{12}$ are the same as in Formula 3.

The liquid crystal compound of Formula 3-1 may have the structure of Formula 3-1-1 or Formula 3-1-2 as follows:

Formula 3-1-1

Formula 3-1-2

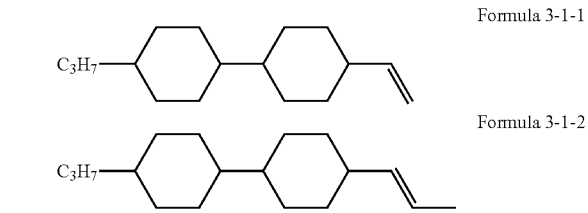

The liquid crystal compound represented as Formula 3, particularly as Formula 3-1-1, has lower viscosity than the liquid crystal compound of Formula 1. Thus, it is possible to compensate for the viscosity of the liquid crystal composition, when combined with the liquid crystal compound of Formula 1. In particular, when the liquid crystal compound of Formula 1 is mixed with the liquid crystal compound of Formula 3-1-1, the liquid crystal compound of Formula 3-1-1 may be included at the concentration of 15-45% by weight with respect to the overall liquid crystal composition. When the liquid crystal compound of Formula 3-1-1 is at the concentration of 15% or lower by weight, it is difficult to obtain a liquid crystal composition with low rotational viscosity for moving pictures, while, when it is at the concentration of higher than 45% by weight, a single substance is used by an excessive amount, and low temperature stability may be reduced.

In the liquid crystal composition according to an embodiment, the liquid crystal compound includes at least one liquid crystal compound of Formula 1, at least one liquid crystal compound of Formula 2, and at least one liquid crystal compound of Formula 3.

In the liquid crystal composition according to an embodiment, the liquid crystal compound may further include at least one compound of the liquid crystal compounds of Formula 4.

Formula 4

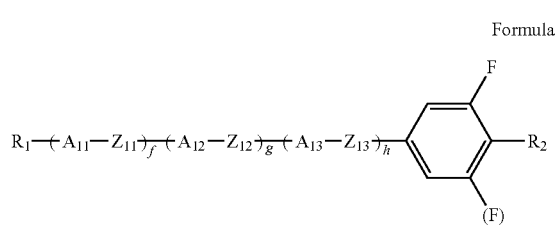

In Formula 4, $R_1$ and $R_2$ are the same as in the definitions of $R_1$ and $R_2$ in Formula 1, $A_{11}$, $A_{12}$, $A_{13}$, $Z_{11}$, $Z_{12}$ and $Z_{13}$ are also the same as in the definitions of $A_{11}$, $A_{12}$, $A_{13}$, $Z_{11}$, $Z_{12}$ and $Z_{13}$ in Formula 1, f, g, and h are independently 0 or 1, and f+g+h is 2 or 3.

The liquid crystal compound of Formula 4 may include at least one of the liquid crystal compounds with the structure represented in Formula 4-1, and $R_1$, $R_2$ in Formula 4-1 are the same as the definitions for Formula 1.

Formula 4-1

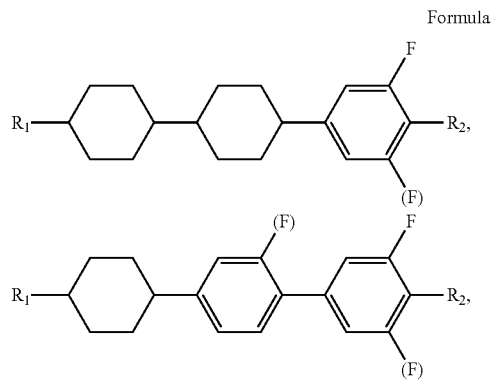

-continued

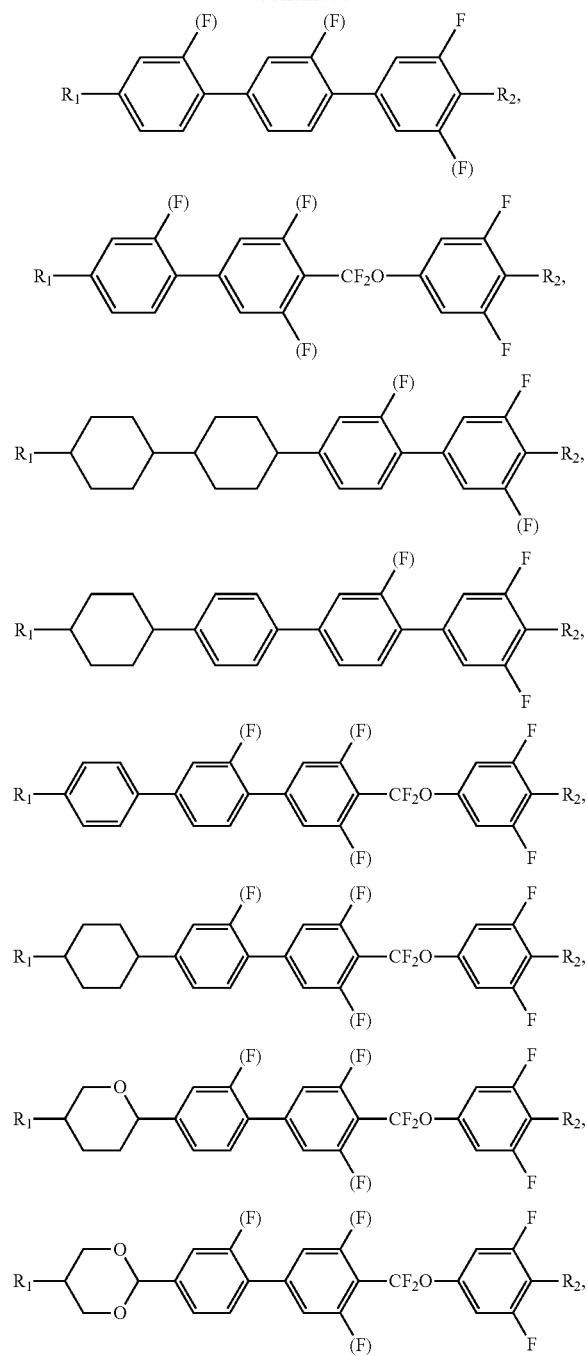

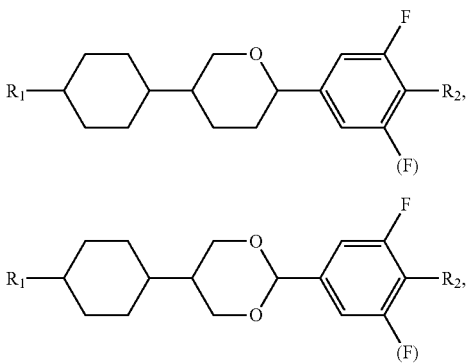

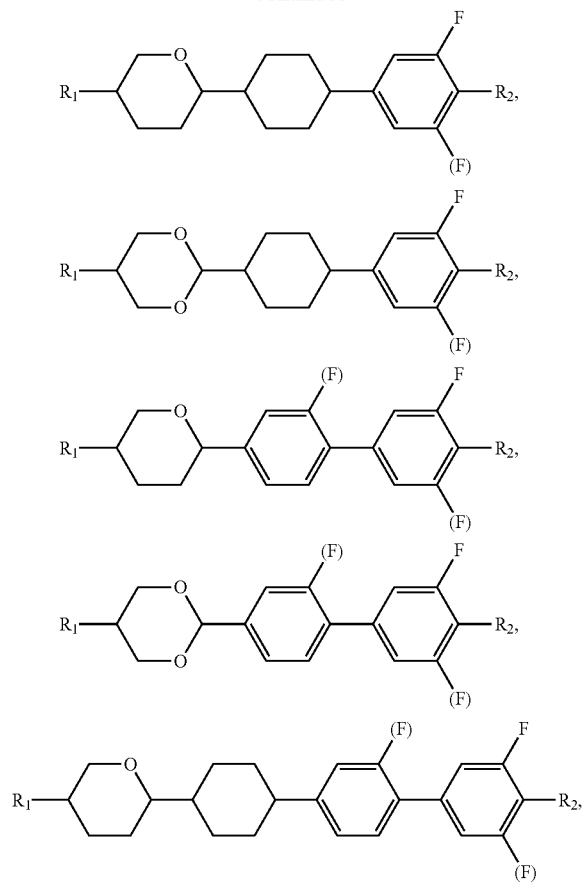

According to an embodiment, the liquid crystal compound of Formula 4-1 includes at least one of the liquid crystal compounds with the structures represented in Formulae 4-1-1 and 4-1-2.

Formula 4-1-1

Formula 4-1-2

A represents one of the following structures:

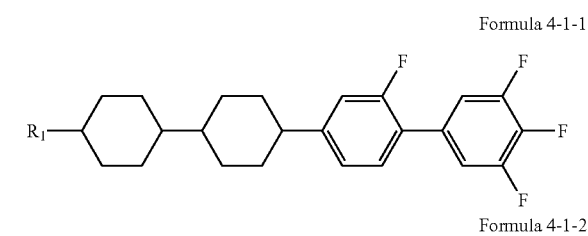

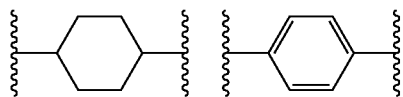

The liquid crystal compound represented as Formula 4 is used for optimizing the physical property of the liquid crystal composition for the liquid crystal display device, and, especially for the compound of Formula 4-1-1 composition, it may improve both the clearing temperature and the dielectric constant of the liquid crystal at the same time. Also, when the liquid crystal composition including Formula 1 has low dielectric anisotropy not greater than 6, low temperature stability may be reduced; however, when the compound of Formula 4-1-1 is included at the concentration of 1-10% by weight with respect to the overall liquid crystal composition, the low temperature stability may be improved.

The liquid crystal compound represented as Formula 4-1-1 may have the structure of Formula 4-1-1-1.

Formula 4-1-1-1

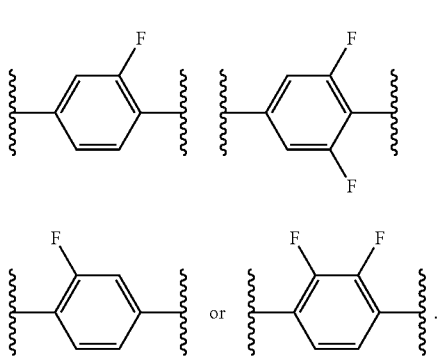

Also, the liquid crystal composition embodiments may further include various additives, for example, an antioxidant and/or an ultraviolet stabilizer.

The liquid crystal composition may further include one or more compounds selected from Formulae 5-7 as the antioxidant or the UV stabilizer.

Formula 5

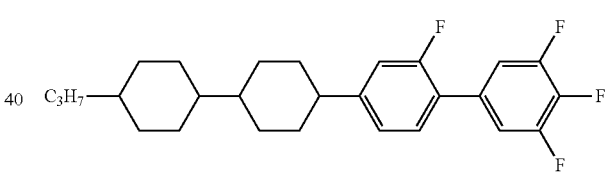

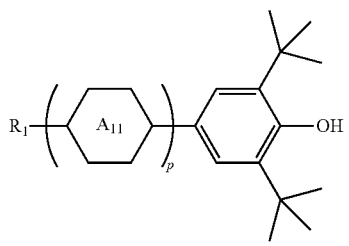

$R_1$ and $A_{11}$ are the same as in the definitions for Formula 1, and p is 0 or 1.

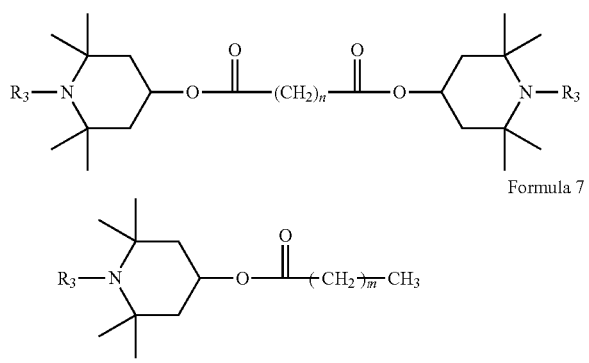

Formula 6

Formula 7

In Formula 7, $R_3$ represents hydrogen, oxygen radical, or an alkyl having 1-15 carbon atoms, in which at least one —$CH_2$— group may be independently replaced by —C≡C—, —$CF_2O$—, —CH=CH—, —O—, —CO—O—, —O—CO— or —O—CO—O— in such a way that no two oxygen atoms bind to each other, 1-3 hydrogen atoms may be replaced by halogen atoms, n is 1-12, and m is 0-12.

The content of the compound selected from Formulae 5-7 may be about 1-2,000 ppm, and, preferably, about 200-500 ppm based on an overall weight of the composition.

The compound of Formula 5 may capture impurities caused by UV within the liquid crystal composition, for example, ions, radicals, etc.

The liquid crystal compound of Formula 5 may be the compound of Formula 5-1.

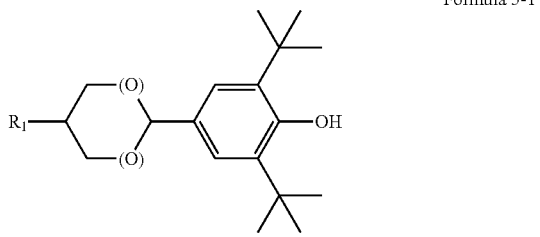

Formula 5-1 wherein (O) is O or $CH_2$.

The compounds of Formulae 6 and 7 may capture impurities caused by heat within the liquid crystal composition, for example, ions, radicals, etc. The liquid crystal composition according to an embodiment includes at least one of the liquid crystal compounds of Formula 1 and the compounds of Formulae 5-7, and, in this case, heat stability and UV stability of the liquid crystal composition are improved by the inclusion of at least one of the compounds of Formulae 5-7.

Also, in the liquid crystal composition according to an embodiment, the liquid crystal composition further includes one pitch modifying compound of Formula 8. $R_1$ is the same as defined for Formula 1.

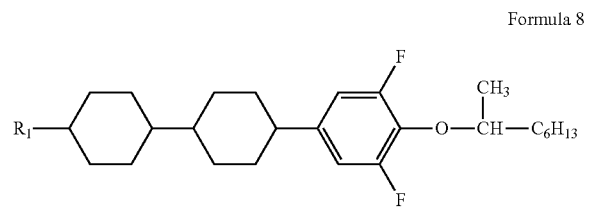

Formula 8

The pitch means, when the liquid crystal has a twisted spiral structure, a distance covered by a director of the liquid crystal in the spiral structure during a rotation of 360°. The pitch value may be modified according to a composition ratio of the pitch modifying agent.

A desired pitch may be more easily obtained when the compound represented as Formula 8 is included at the concentration of about 0.01-5% by weight with respect to the liquid crystal composition 100% by weight.

According to an embodiment, the liquid crystal composition includes various combinations of one of the liquid crystal compounds of Formulae 1-4 and/or one of the liquid crystal compounds of Formulae 5-8.

For example, the liquid crystal composition according to an embodiment may include the liquid crystal compound of Formula 1-2 and the liquid crystal compound of Formula 2-1.

The liquid crystal composition according to another embodiment includes the liquid crystal compound of Formula 1-2 and the liquid crystal compound of Formula 2-2.

The liquid crystal composition according to still another embodiment includes the liquid crystal compound of Formula 1-2 and the liquid crystal compound of Formula 4-1.

The liquid crystal composition according to still another embodiment additionally includes the liquid crystal compound of Formula 3. For example, the liquid crystal composition according to an embodiment may include the liquid crystal compound of Formula 1-2, the liquid crystal compound of Formula 2-2, and the liquid crystal compound of Formula 3.

The liquid crystal composition according to still another embodiment additionally includes the liquid crystal compound of Formula 4.

The liquid crystal composition according to still another embodiment additionally includes at least one of the liquid crystal compounds of Formulae 5-7. For example, the liquid crystal composition according to an embodiment may include a liquid crystal compound of Formula 1-2 and the liquid crystal compounds of Formulae 5-7.

The liquid crystal composition according to still another embodiment further includes the compound of Formula 8.

According to an embodiment, the liquid crystal composition may have various composition ratios without departing from the concept of the present disclosure.

According to an embodiment, the liquid crystal composition comprises a liquid crystal compound of Formula 1-2, a liquid crystal compound of Formula 3-1-1, and a liquid crystal compound of Formula 5.

For example, the liquid crystal composition according to an embodiment may include 3-35 parts by weight of the liquid crystal compound represented as Formula 1-2-2, 15-45 parts by weight of the liquid crystal compound represented as Formula 3-1-1, and 0.01-0.05 parts by weight of the liquid crystal compound represented as Formula 5.

Also, the liquid crystal composition according to an embodiment may include the liquid crystal compound represented as Formula 1-2-2 and the liquid crystal compound represented as Formula 1-2-3, and, in this case, the weight ratio between the liquid crystal compound of Formula 1-2-2 and the liquid crystal compound of Formula 1-2-3 may be 1:0.5-1:2.0.

According to an embodiment, the liquid crystal composition comprises a liquid crystal compound of Formula 1-2, a liquid crystal compound of Formula 2-1-1-1, a liquid crystal compound of Formula 2-1-1-2, and a liquid crystal compound of Formula 4-1-1-1.

Also, the liquid crystal composition according to an embodiment includes 5-20 parts by weight of at least one of the liquid crystal compounds represented as Formula 1-2 and the liquid crystal compound represented as Formula 2-1-1-1, 5-20 parts by weight of the liquid crystal compound represented as Formula 2-1-1-2, and 2-10 parts by weight of the liquid crystal compound represented as Formula 4-1-1-1.

According to an embodiment, the liquid crystal composition comprises a liquid crystal compound of Formula 1-2, a liquid crystal compound of Formula 3-1-1, a liquid crystal compound of Formula 2-2-1-1, and a liquid crystal compound of Formula 4-1-2.

Also, the liquid crystal composition according to an embodiment includes liquid crystal compound 1-2, 15-45 parts by weight of the liquid crystal compound represented as Formula 3-1-1, 2-15 parts by weight of the liquid crystal compound represented as Formula 2-2-1-1, and 3-35 parts by weight of the liquid crystal compound represented as Formula 4-1-2.

In this manner, a liquid crystal composition with positive dielectric anisotropy may be obtained, and a there is obtained a liquid crystal composition with dielectric anisotropy of 2.0 or more, a clearing temperature of 70 degrees or higher, and refractive index anisotropy of 0.09 or more. The liquid crystal composition may be used as the liquid crystal for an active matrix (AM)-LCD or a passive matrix (PM)-LCD). And the liquid crystal composition may be applied to a liquid crystal display of a vertical electric field mode or a horizontal electric field mode, and, more specifically, to various LCD modes such as twist nematic (TN), super-twisted nematic (STN), in-plane switching (IPS), fringe field switching (FFS), plane to line switching (PLS), an advanced high-performance IPS (AH-IPS)), polymer sustained alignment (PSA) etc.

The liquid crystal display to which the liquid crystal composition according to an embodiment is applied may have a vertical electric field mode or a horizontal electric field mode.

Liquid Crystal Display Device

FIG. 1 is a diagram illustrating a liquid crystal display device according to one embodiment.

The liquid crystal display device according to an embodiment may be implemented in various modes, for example, twist nematic (TN), super-twisted nematic (STN), in-plane switching (IPS), fringe field switching (FFS), plane to line switching (PLS), an advanced high-performance IPS (AH-IPS)), polymer sustained alignment (PSA) modes, etc.

In one embodiment, the TN mode is explained as an example, and the arrangement and shapes of respective components may be varied according to the respective modes.

According to an embodiment, the liquid crystal display device 100 includes a first substrate 110, a second substrate 120, and a liquid crystal layer 130 which is interposed between the first substrate 110 and the second substrate 120. A plurality of pixel areas are defined on the second substrate 120 and a plurality of pixels are provided on each of the pixel areas.

The first substrate 110 may include an upper base substrate 111, a light shielding layer 112, a color filter 113, an upper insulation film 114, a common electrode 115, and an upper alignment film 101. The light shielding layer 112 is formed on the upper base substrate 111 and may include a colorant which is an opaque material with low optical transmittance, for example, carbon black etc.

The color filter 113 is formed on the upper base substrate 111 and may be formed to be partially overlapped with the light shielding layer 112 or other adjacent color filter 113.

The insulation film 114 protects the light shielding layer 112 and the color filter 113, and compensates for a step difference generated by the light shielding layer 112 and the color filter 113 to planarize a surface of the first substrate 110.

The common electrode 115, for example, may be made of indium tin oxide (ITO) or indium zinc oxide (IZO) etc. A predetermined common voltage is applied on the common electrode 114.

The upper alignment film 101 touches the liquid crystal layer 130 such that the liquid crystal molecules 131 in the liquid crystal layer 130 are initially aligned or slanted in a predetermined direction.

The second substrate 120 includes a plurality of thin film transistors which are provided for the pixels. More specifically, the second substrate 120 may include a lower base substrate 121, a gate electrode 122, a gate insulation film 123, a semiconductor layer 124a, an ohmic contact layer 124b, a source electrode 125, a drain electrode 126, a passivation layer 127, a pixel electrode 128, and a lower alignment film 102.

The gate electrode 122 is formed on the lower base substrate 121 and receives a gate signal from a gate line (not shown). The gate insulation film 123 covers the gate electrode 122.

The semiconductor layer 124a is formed on the gate insulation film 123 to overlap the gate electrode 122, and a pair of ohmic contact layers 124b is formed on the semiconductor layer 124a to be apart from each other.

The source electrode 125 and the drain electrode 126 are formed on the ohmic contact layer 124b. The source electrode 125 is arranged to be apart from the drain electrode 126 such that a portion of the semiconductor layer 124a is exposed. A portion of the drain electrode 126 is electrically connected to the pixel electrode 128 via a contact hole (CH).

The passivation layer 127 covers the source electrode 125, the drain electrode 126, and the exposed semiconductor layer 124a.

The contact hole (CH) is formed on the passivation layer 127 such that the drain electrode 126 is electrically connected to the pixel electrode 128 through the contact hole.

The pixel electrode 128 is formed on the passivation layer 127, and a lower alignment film 102 is formed on the pixel electrode 128. A predetermined data voltage, which is delivered from the drain electrode 126, is applied to the pixel electrode 128.

A voltage difference between the data voltage and the common voltage applied on the common electrode 115 generates an electric field, and the arrangement of the liquid crystal molecules 131 in the liquid crystal layer 130 may be adjusted by the electric field.

According to an embodiment, although the light shielding layer and the color filter are illustrated to be formed on the upper base substrate, the present disclosure is not limited to this, and the light shielding layer and/or the color filter may be formed on the lower base substrate.

Figure 2:
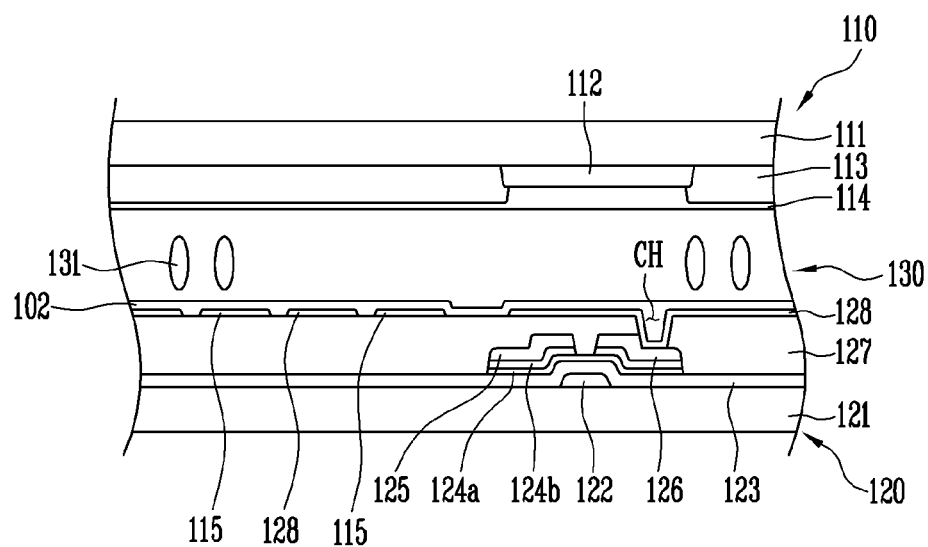
FIG. 2 is a diagram illustrating a liquid crystal display device according to another embodiment.

Also, according to an embodiment, when an electrode part refers to electrodes which provide the electric field to the liquid crystal layer, that is, the pixel electrodes and the common electrodes, the electrode part may be provided in various manners. For example, although the common electrode is illustrated to be formed on the upper base substrate in the aforementioned embodiment, the present disclosure is not limited to this, and the common electrode may be formed on the lower base substrate in other embodiments. FIG. 2 is a diagram illustrating a liquid crystal display device according to another embodiment. In the embodiment, the common electrode 115 is provided on the lower base substrate 121. In this embodiment, the common electrode 115 is on the same layer with the pixel electrode 128, but not limited thereto. The common electrode 115 may be provided on a different layer from the pixel electrode 128 and may overlap the pixel electrode 128 in this embodiment.

The liquid crystal layer 130 includes the liquid crystal composition including the liquid crystal compound of Formula 1. Since the liquid crystal composition is substantially same as the liquid crystal composition according to an embodiment described in the above, no further description will be given.

In order to increase a viewing angle, the pixels may be divided into a plurality of domains, and the liquid crystal composition may be aligned in two or more different directions in one pixel area. Bumps, etc. may be formed in the respective pixels in order to divide the pixels into a plurality of domains, and the pixel electrode and the common electrode may include cut portions.

The liquid crystal display device to which the liquid crystal composition according to an embodiment is applied may have various modes such as vertical electric field modes (e.g.: TN, STN, VA etc.) as well as horizontal electric field modes (e.g.: IPS, PLS, FFS etc.).

In the following, embodiments will be explained in detail.

Synthesis of Liquid Crystal Compound of Formula 1

The liquid crystal compound of Formula 1 may be synthesized using the synthesis method as follows, and what is important for the corresponding synthesis method is to introduce a methyl group beside fluorine.

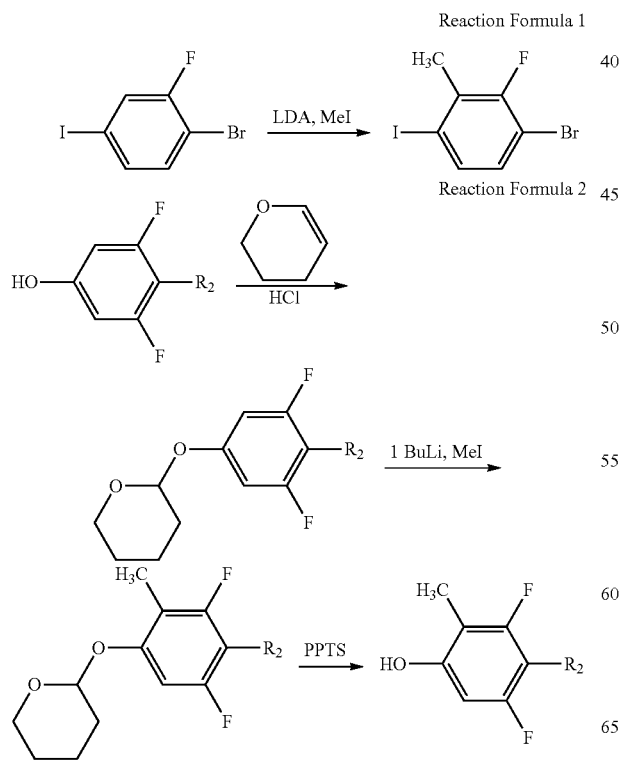

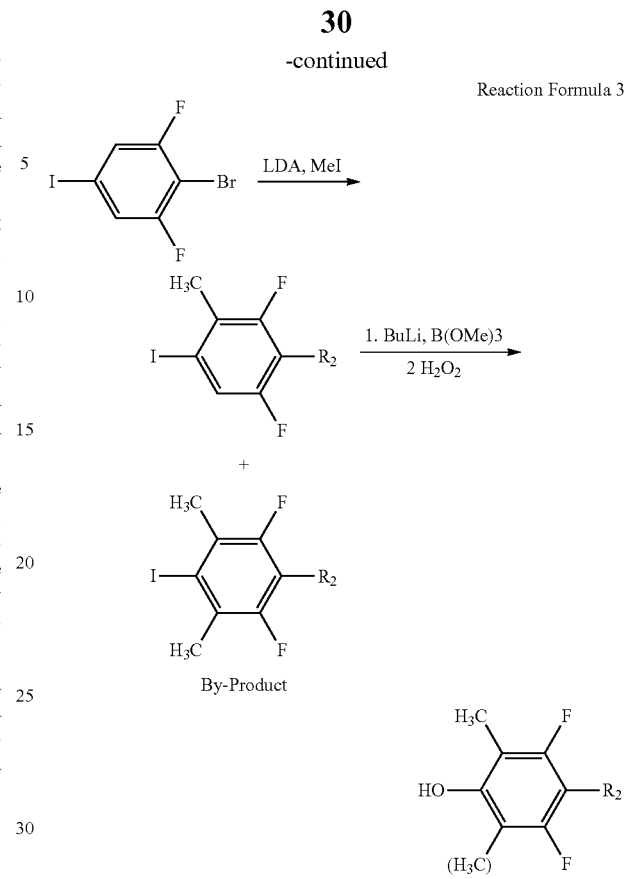

As shown in Reaction Formula 1, a methyl group may be attached to a third location in phenylene by removing hydrogen from the third location of 2-fluoro-1,4-phenylene by using lithium diisopropylamide (LDA) and then adding methyl iodide thereto in a dropwise manner. This reaction may be acknowledged in the reference document ((a) Schlosser, M. 2001 *Eur. J. Org. Chem.*, pp 3975; (b) Schlosser, M. (2005) *Angew. Chem. Int. Ed.*, vol 44, pp 376).

On the other hand, according to Reaction Formula 3, which applies the method of Reaction Formula 1 to 2,6-fluoro-1,4-phenylene, a compound is generated with one or two methyl groups substituted. Since this compound has no polarity, it is inseparable, and, as a result, it is not possible to obtain a desired composition.

As a most effective method, an alcohol portion is protected in a ring structure as in Reaction Formula 2, and butyl lithium is added, such that a methyl group is introduced only to a single position. This alcohol ring structure protection reaction is performed by using a known method, and the alcohol ring structure protection material was obtained according to the present disclosure by mixing 1.5 equivalent weight of 2,3-dihydropyran with the alcohol compound and by using hydrochloric acid as a catalyst.

Therefore, the liquid crystal composition as follows may be made by using Reaction Formulae 1 and 2, and functional groups not disclosed in Reaction Formulae 1-3 may be synthesized by using a known method.

Detailed examples of the liquid crystal composition according to an embodiment which may be made by using aforementioned Reaction Formulae are as follows, and $R_1$ is the same as in Formula 1:

[1] 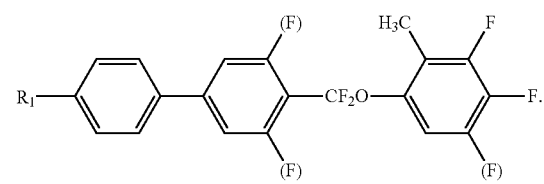
[2] 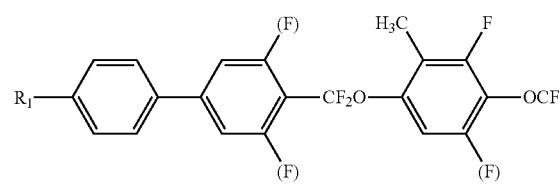
[3] 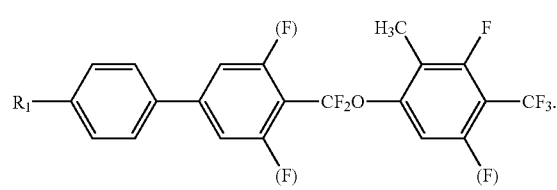
[4] 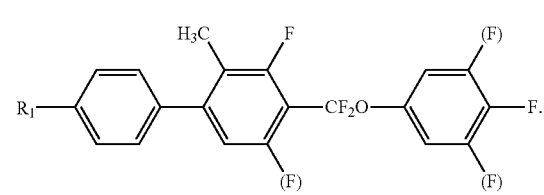
[5] 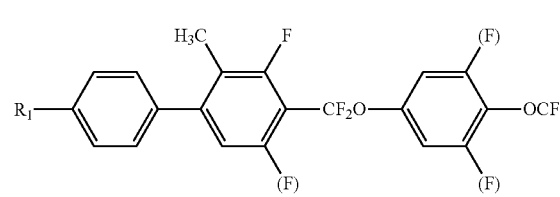
[6] 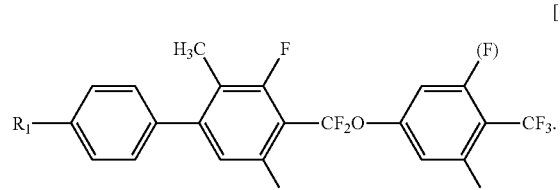
[7] 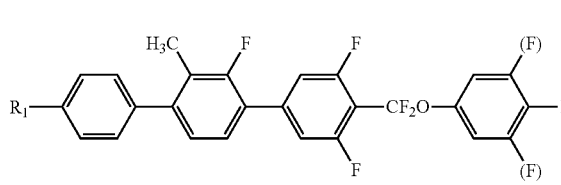
[8] 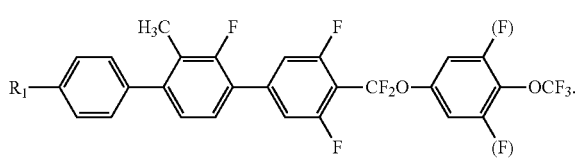
-continued
[9] 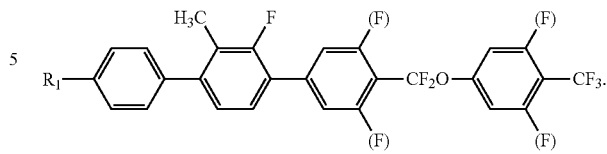
[10] 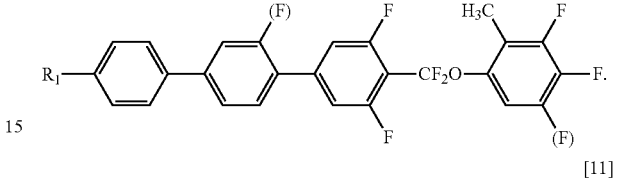
[11] 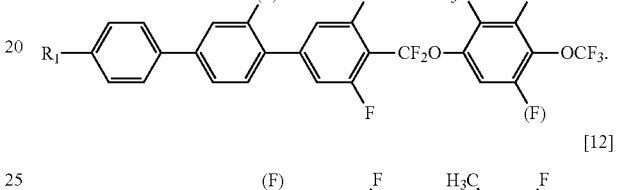
[12] 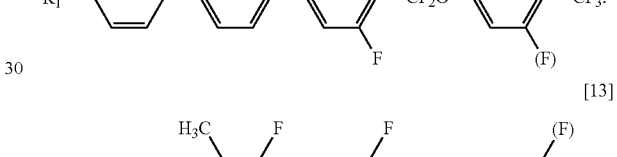
[13] 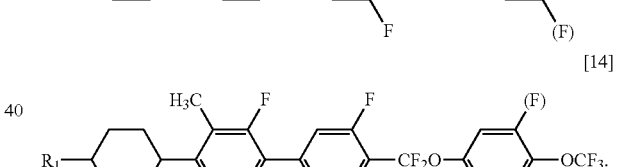
[14] 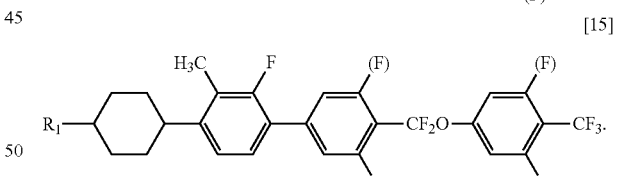
[15] 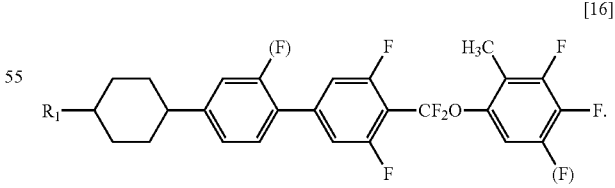
[16] 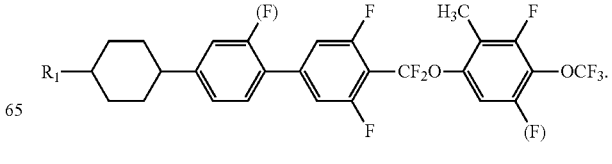
[17]

In the following, functions and effects of the present invention will be explained in detail by means of detailed embodiments. However, these embodiments are provided as mere examples, and these do not delimit the scope of the present disclosure.

Synthesis Example 1: Synthesis of Liquid Crystal Compound A1

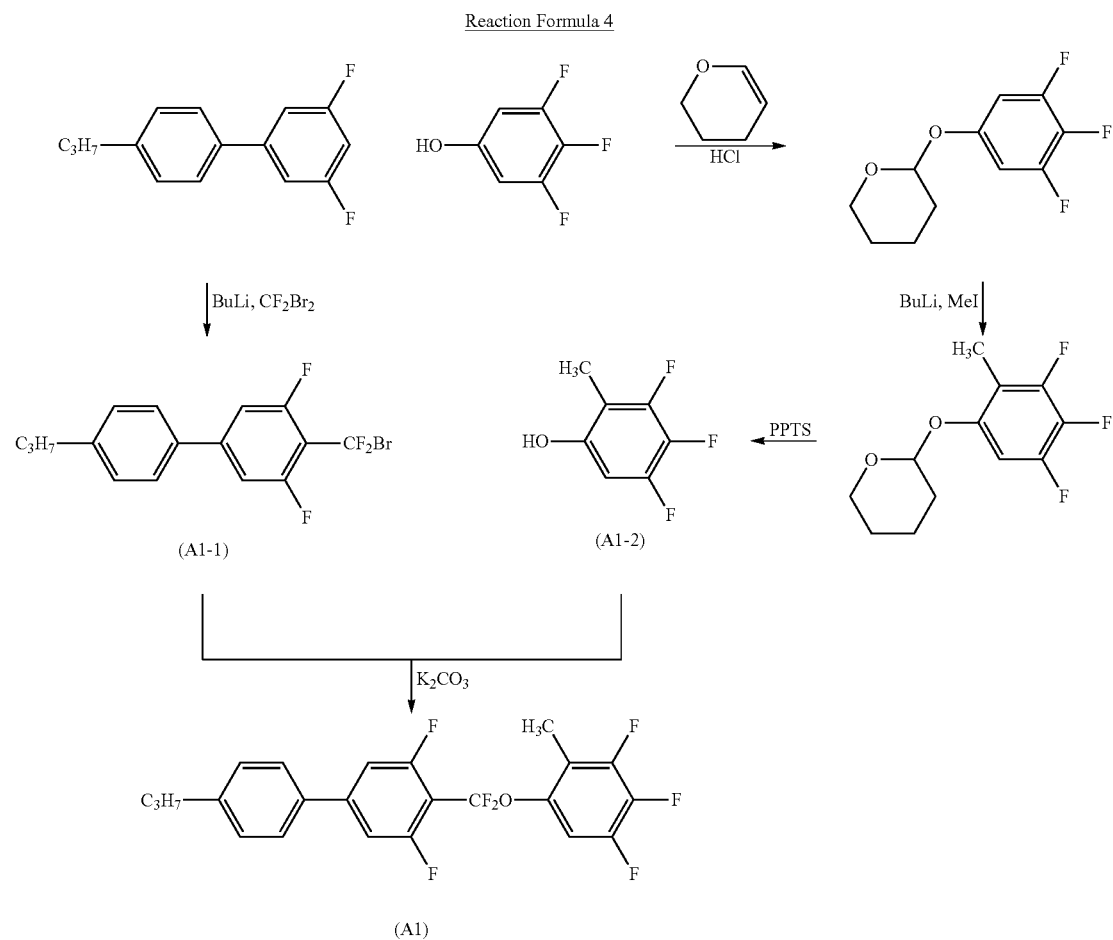

Under nitrogen atmosphere, an alcohol compound (A1-2) (2.3 g, 14.2 mmol), tetrabutylammonium bromide (0.42 g, 1.29 mmol) and potassium carbonate (3.6 g, 25.9 mmol) were dissolved into dimethylformamide (50 ml), and the result was stirred for 1 hour at 40° C. A bromine compound (A1-1) (5.4 g, 15 mmol) was dissolved in dimethylformamide (50 ml), the solution was dropped, and then the result was refluxed for 2 hours at 90° C. After the reaction was over, the reaction solution was diluted with water and toluene, such that phases are separated. An organic layer was extracted, cleansed with sodium bicarbonate aqueous solution and distilled water, and then dried on magnesium sulfate. The result was eluted on a silica gel column, and then recrystallized (solvent n-hexane:ethyl acetate) to yield a product (A1) (4.5 g, 10.3 mol). (yield 73%) Mass spectrum: 252, 281, 442[M$^+$] transition temperature (T$_{Cr-I}$): 67.3° C.

Synthesis Example 2: Synthesis of Liquid Crystal Compound A2

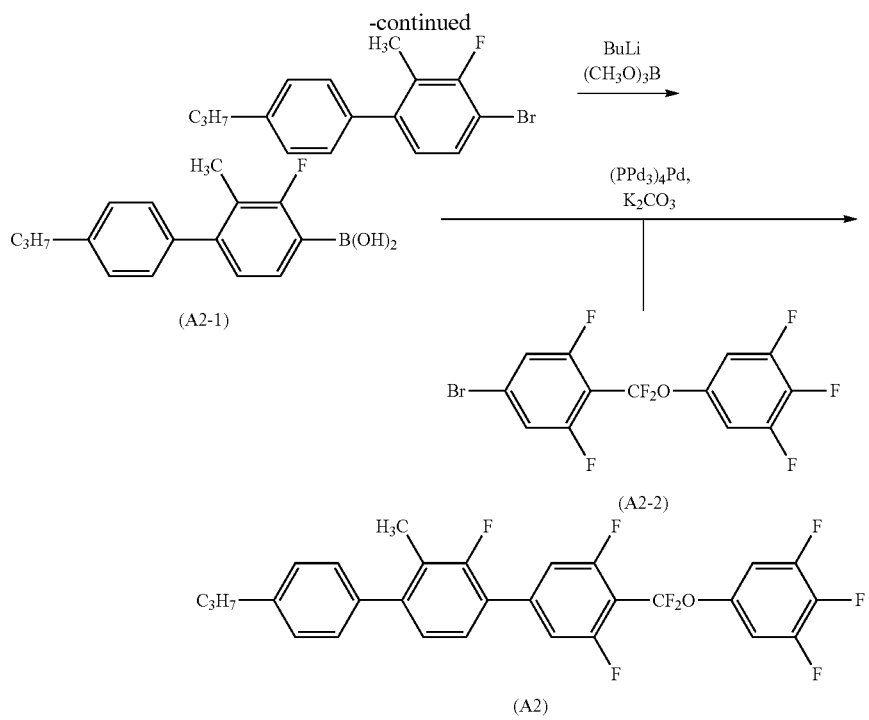

Under nitrogen atmosphere, a boronic acid compound (A2-1) (4.9 g, 20 mmol), a bromine compound (A2-2) (7.8 g, 20 mmol), and $(PPh_3)_4Pd$ (0.1 g) was dissolved in dimethoxy ethane (100 ml), and then, 2 M potassium carbonate aqueous solution (30 ml) was added. The temperature was raised to 60° C., and the result was refluxed for 6 hours. After cooling, the reaction solution was diluted with water and dichloromethane, and phases were separated. Then, an organic layer was extracted, cleansed with distilled water, and dried on magnesium sulfate. The result was eluted on a silica gel column, and recrystallized (solvent n-hexane:ethyl acetate) to yield a product (A2) (4.8 g, 8.9 mmol). (yield 45%) Mass spectrum 360, 389, 536[M$^+$], transition temperature $(T_{Cr\text{-}I})$: 53.1° C.

Synthesis Example 3: Synthesis of Liquid Crystal Compound A3

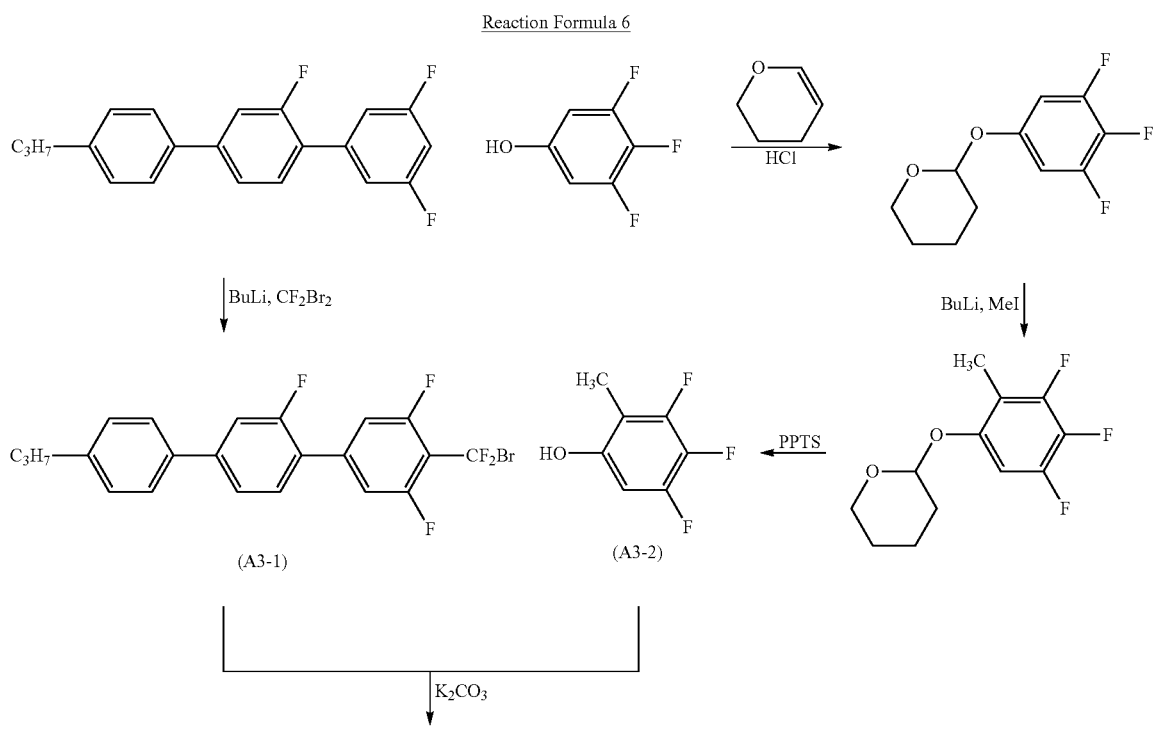

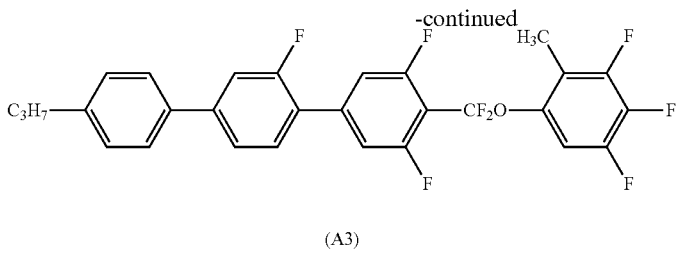

(A3)

Under nitrogen atmosphere, an alcohol compound (A3-2) (4.1 g, 25.6 mmol), tetrabutylammonium bromide (0.75 g, 2.3 mmol) and potassium carbonate (6.4 g, 46.6 mmol) were dissolved into dimethylformamide (70 ml), and the result was stirred for 1 hour at 40° C. A bromine compound (A3-1) (12.2 g, 27 mmol) was dissolved in dimethylformamide (70 ml), the solution was dropped, and then the result was refluxed for 2 hours at 90° C. After the reaction was over, the reaction solution was diluted with water and toluene, such that phases are separated. An organic layer was extracted, cleansed with sodium bicarbonate aqueous solution and distilled water, and then dried on magnesium sulfate. The result was eluted on a silica gel column, and then recrystallized (solvent n-hexane:ethyl acetate) to yield a product (A3) (9.7 g, 18.1 mol). (yield 71%) Mass spectrum: 346, 375, 536[M$^+$] transition temperature (T$_{Cr-N}$): 70.2° C., transition temperature (T$_{N-I}$): 126.3° C.

Synthesis Example 4: Synthesis of Liquid Crystal Compound A4

Reaction Formula 7

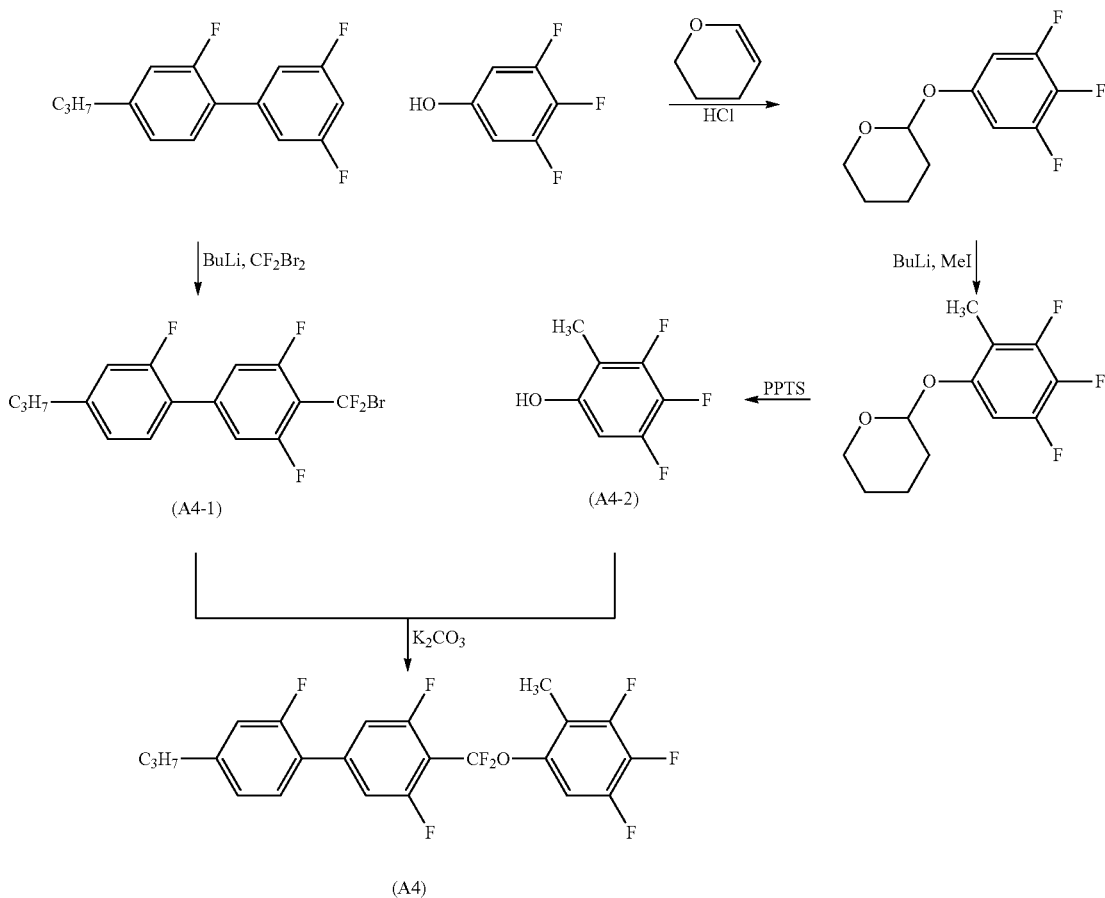

(A4)

Under nitrogen atmosphere, an alcohol compound (A4-2) (3.20 g, 19.7 mmol), tetrabutylammonium bromide (0.64 g, 2.0 mmol) and potassium carbonate (5.46 g, 39.5 mmol) were dissolved into dimethylformamide (50 ml), and the result was stirred for 1 hour at 40° C. A bromine compound (A4-1) (8.23 g, 21.7 mmol) was dissolved in dimethylformamide (50 ml), the solution was dropped, and then the result was refluxed for 2 hours at 90° C. After the reaction was over, the reaction solution was diluted with water and toluene, such that phases are separated. An organic layer was extracted, cleansed with sodium bicarbonate aqueous solution and distilled water, and then dried on magnesium sulfate. The result was eluted on a silica gel column, and then recrystallized (solvent n-hexane:ethyl acetate) to yield a product (A4) (5.91 g, 12.8 mmol). (yield 65%) Mass spectrum: 271, 299, 460[M⁺] transition temperature ($T_{Cr-I}$) 72.2° C.

Synthesis Example 5: Synthesis of Liquid Crystal Compound A5 result was refluxed for 2 hours at 90° C. After the reaction was over, the reaction solution was diluted with water and toluene, such that phases are separated. An organic layer was extracted, cleansed with sodium bicarbonate aqueous solution and distilled water, and then dried on magnesium sulfate. The result was eluted on a silica gel column, and then recrystallized (solvent n-hexane:ethyl acetate) to yield

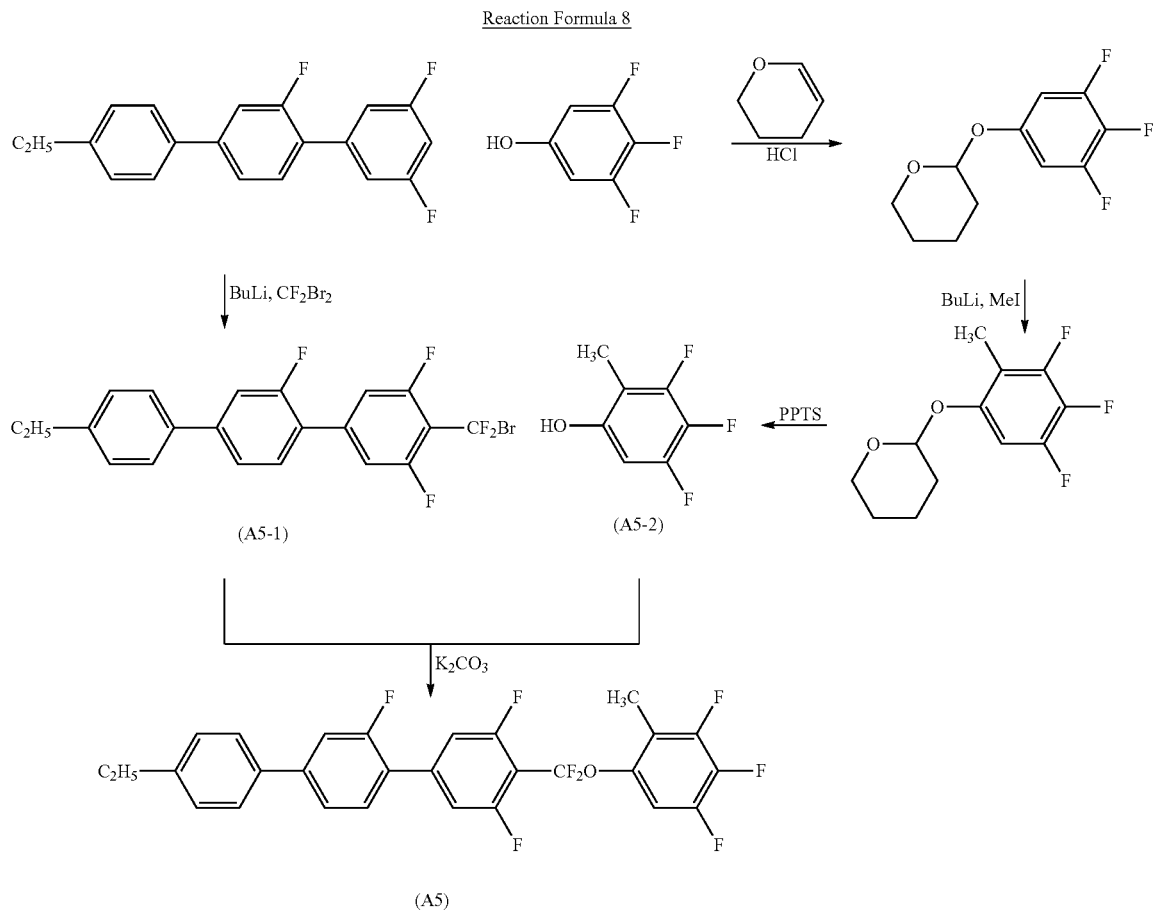

Reaction Formula 8

Under nitrogen atmosphere, an alcohol compound (A5-2) (3.70 g, 22.8 mmol), tetrabutylammonium bromide (0.74 g, 2.3 mmol) and potassium carbonate (6.31 g, 45.6 mmol) were dissolved into dimethylformamide (50 ml), and the result was stirred for 1 hour at 40° C. A bromine compound (A5-1) (11.08 g, 25.1 mmol) was dissolved in dimethylformamide (50 ml), the solution was dropped, and then the a product (A5) (8.59 g, 16.4 mmol). (yield 72%) Mass spectrum: 347, 361, 522[M⁺] transition temperature ($T_{Cr-N}$) 89° C., transition temperature ($T_{N-I}$): 123.0° C.

Synthesis Example 6: Synthesis of Liquid Crystal Compound A6

Reaction Formula 9

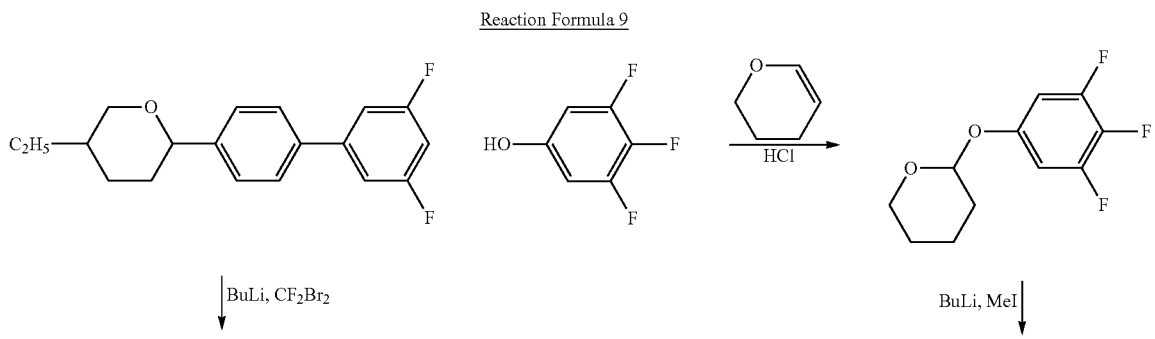

-continued

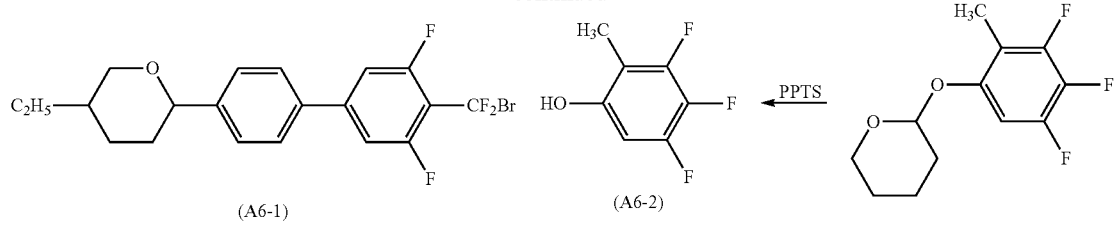

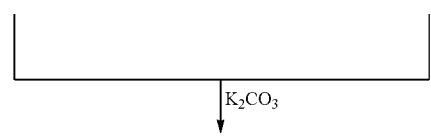

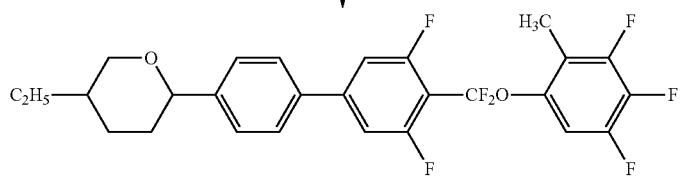

Under nitrogen atmosphere, an alcohol compound (A6-2) (2.27 g, 14.0 mmol), tetrabutylammonium bromide (0.46 g, 1.4 mmol) and potassium carbonate (3.87 g, 28.0 mmol) were dissolved into dimethylformamide (50 ml), and the result was stirred for 1 hour at 40° C. A bromine compound (A6-1) (6.64 g, 15.4 mmol) was dissolved in dimethylformamide (50 ml), the solution was dropped, and then the result was refluxed for 2 hours at 90° C. After the reaction was over, the reaction solution was diluted with water and toluene, such that phases are separated. An organic layer was extracted, cleansed with sodium bicarbonate aqueous solution and distilled water, and then dried on magnesium sulfate. The result was eluted on a silica gel column, and then recrystallized (solvent n-hexane:ethyl acetate) to yield a product (A6) (4.23 g, 8.3 mmol). (yield 59%) Mass spectrum: 351, 512[M$^+$] transition temperature (T$_{Cr-N}$): 82.4° C., transition temperature (T$_{N-I}$): 94.5° C.

Synthesis Example 7: Synthesis of Liquid Crystal Compound A7

Reaction Formula 10

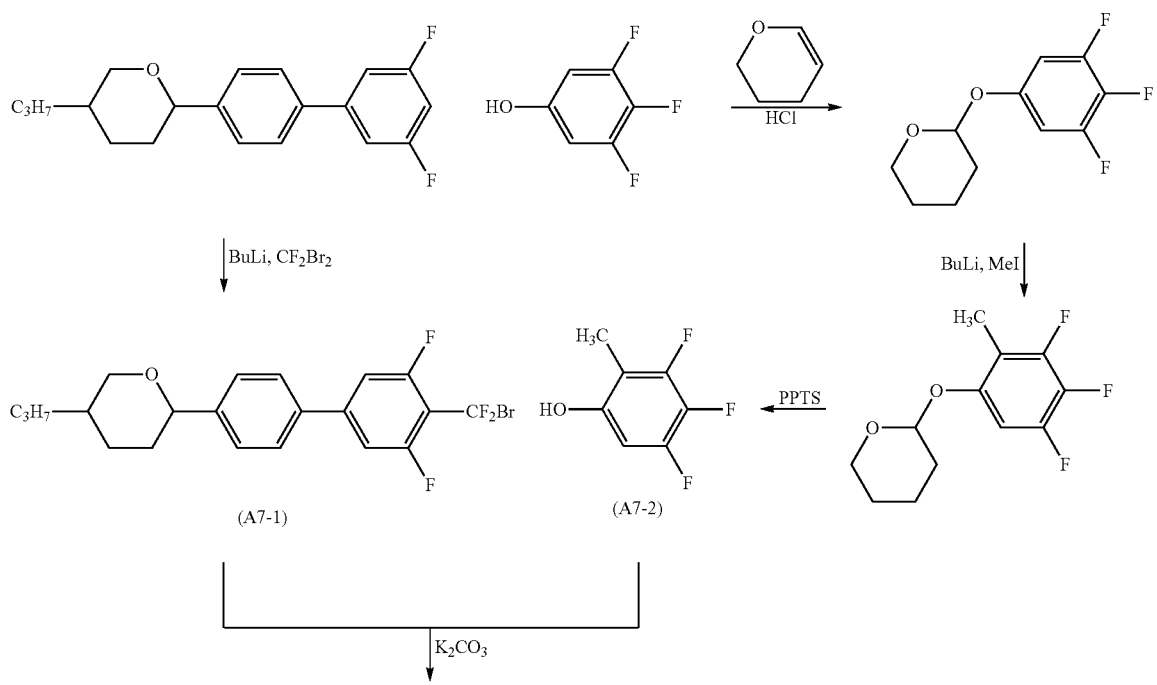

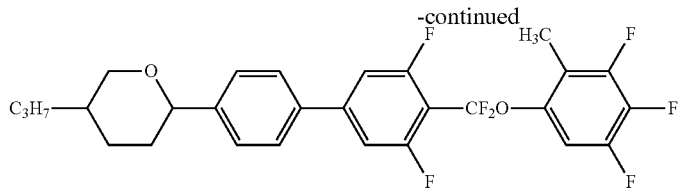

(A7)

Under nitrogen atmosphere, an alcohol compound (A7-2) (3.25 g, 20.0 mmol), tetrabutylammonium bromide (0.65 g, 2.0 mmol) and potassium carbonate (5.54 g, 40.1 mmol) were dissolved into dimethylformamide (50 ml), and the result was stirred for 1 hour at 40° C. A bromine compound (A7-1) (9.82 g, 22.1 mmol) was dissolved in dimethylformamide (50 ml), the solution was dropped, and then the result was refluxed for 2 hours at 90° C. After the reaction was over, the reaction solution was diluted with water and toluene, such that phases are separated. An organic layer was extracted, cleansed with sodium bicarbonate aqueous solution and distilled water, and then dried on magnesium sulfate. The result was eluted on a silica gel column, and then recrystallized (solvent n-hexane:ethyl acetate) to yield a product (A7) (6.44 g, 12.2 mmol). (yield 61%) Mass spectrum: 365, 526[$M^+$] transition temperature ($T_{Cr-N}$): 65.7° C., transition temperature ($T_{N-I}$): 121.8° C.

Synthesis Example 8: Synthesis of Liquid Crystal Compound A8

Reaction Formula 11

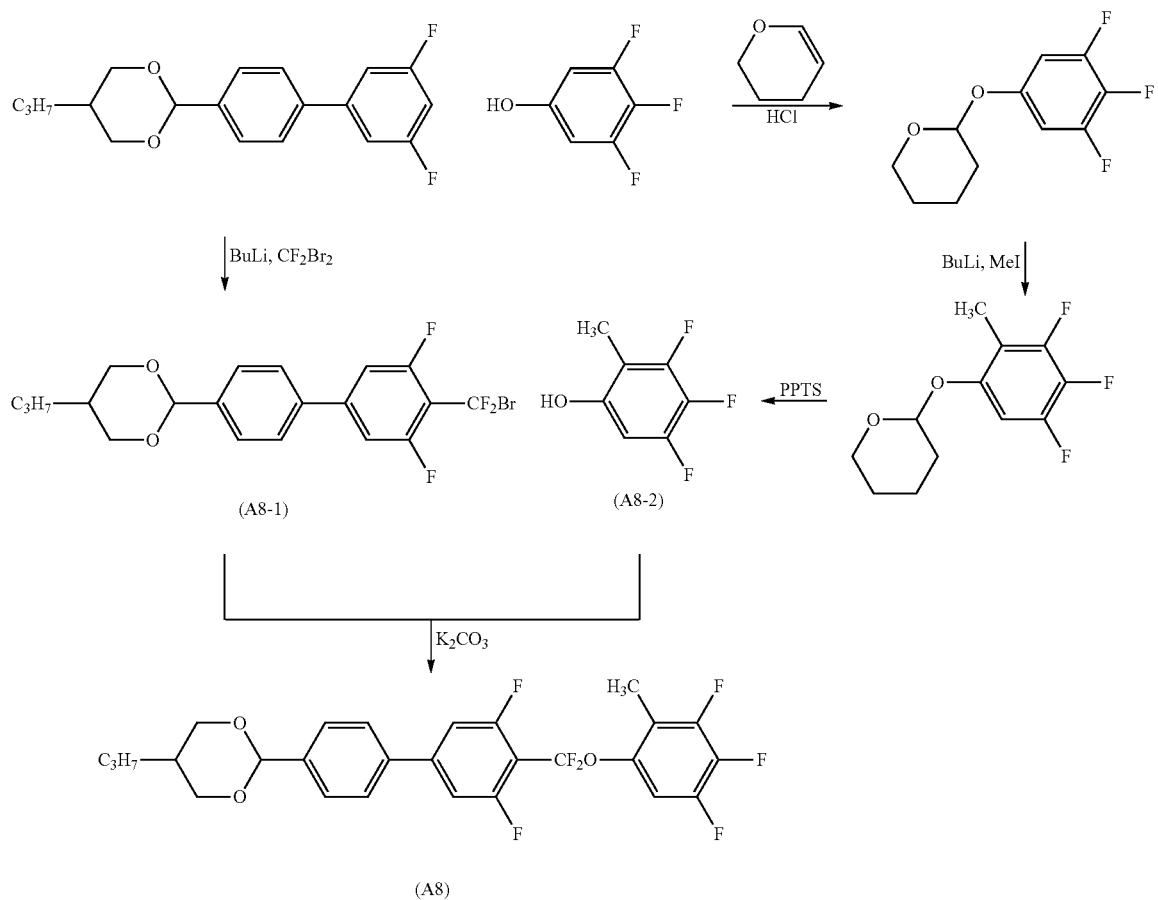

Under nitrogen atmosphere, an alcohol compound (A8-2) (2.74 g, 16.9 mmol), tetrabutylammonium bromide (0.55 g, 1.7 mmol) and potassium carbonate (4.67 g, 33.8 mmol) were dissolved into dimethylformamide (50 ml), and the result was stirred for 1 hour at 40° C. A bromine compound (A8-1) (8.32 g, 18.6 mmol) was dissolved in dimethylformamide (50 ml), the solution was dropped, and then the result was refluxed for 2 hours at 90° C. After the reaction was over, the reaction solution was diluted with water and toluene, such that phases are separated. An organic layer was extracted, cleansed with sodium bicarbonate aqueous solution and distilled water, and then dried on magnesium sulfate. The result was eluted on a silica gel column, and then recrystallized (solvent n-hexane:ethyl acetate) to yield a product (A8) (6.07 g, 11.5 mmol). (yield 68%) Mass spectrum: 367, 528[M⁺] transition temperature ($T_{Cr-N}$): 67.3° C.

Liquid Crystal Compound and Liquid Crystal Composition Evaluation Method

The low temperature stability and the physical property of the liquid crystal compound and the liquid crystal composition were evaluated according to the following method:

(1) Low Temperature Stability

First, 2 g of liquid crystal compound was placed in a 10 mL vial, which was contained in a freezer at −25° C., and recrystallization was checked at an interval of 1 day. When the recrystallization occurred after 00 days from the initial date of storage in the freezer, it is marked as "00 days NG", while it is marked as "20 days OK" when the liquid crystal phase was maintained for 20 days or longer.

(2) Clearing Temperature (Tc)

A drop of the liquid crystal composition whose clearing temperature was to be measured was dropped on a slide glass, and the result was covered with a cover glass to obtain a sample for measuring the clearing temperature.

The sample was put in a device having a METTLER TOLEDO FP90 temperature adjuster, and a change in the sample was observed while increasing the temperature at a speed of 3° C./min using an FP82 HT Hot stage. A temperature at which a hole was formed in the sample was recorded, and the procedure was repeated 3 times to obtain an average value. Then, the value was defined as the clearing temperature of the liquid crystal composition.

(3) Refractive Index Anisotropy (n)

The refractive index (n) of the liquid crystal composition was measured by using the light of a wavelength of 589 nm at 20° C. with an Abbe's refractometer equipped with a polarizing plate mounted on an eyepiece. A surface of a main prism was rubbed in one direction, and the liquid crystal composition to be measured was dropped on the main prism. Then, the refractive index (n∥) when the polarization direction was parallel with the rubbing direction and the index (n⊥) when the polarization direction was perpendicular to the rubbing direction were measured. And, the refractive index values were applied to Equation 1 to measure the refractive index anisotropy (n).

$$n = n\| - n\bot \quad \text{(Equation 1)}$$

(4) Dielectric Anisotropy (Δ∈)

The dielectric constant anisotropy (∈) of the liquid crystal composition was calculated by applying the measured ∈∥∈⊥ to Equation 2.

$$\Delta\in = \in\| - \in\bot \quad \text{(Equation 2)}$$

1. Measurement of the dielectric constant ∈∥: A vertical alignment film was formed by applying a vertical alignment agent to surfaces where ITO patterns of two glass substrates were formed. A spacer was applied on one substrate of the glass substrates such that the vertical alignment films faced each other and a spacing (cell gap) between the two glass substrates was 4 μm, and, then, the two glass substrates were bound into one element. And, the liquid crystal composition to be measured was injected into this element and enclosed with an adhesive using UV for hardening. Then, the dielectric constant of the element (∈∥) at 1 kHz, 0.3 V, and 20° C. was measured by using equipment 4294A manufactured by Agilent.

2. Measurement of the dielectric constant ∈⊥: A horizontal alignment film was formed by applying a horizontal alignment agent to surfaces where ITO patterns of two glass substrates were formed. A spacer was applied on one substrate of the glass substrates such that the horizontal alignment films faced each other and a spacing (cell gap) between the two glass substrates was 4 μm, and, then, the two glass substrates were bound into one element. Then the liquid crystal composition to be measured was injected into this element and enclosed with an adhesive which was hardened by UV. Then, the dielectric constant (∈⊥) of the element at 1 kHz, 0.3 V, and 20° C. was measured by using equipment 4294A manufactured by Agilent.

(5) Rotational Viscosity (γ1)

A horizontal alignment film was formed by applying a horizontal alignment agent to surfaces where ITO patterns of two glass substrates were formed. A spacer was applied on one substrate of the glass substrates such that the horizontal alignment films faced each other and a spacing (cell gap) between the two glass substrates was 20 μm, and, then, the two glass substrates were bound into one element. Then, the liquid crystal composition was injected into this element and enclosed. Then, the rotational viscosity of the element at 20° C. was measured by using equipment model 6254 manufactured by Toyo Corp. equipped with temperature controller (Model SU-241) equipment manufactured by ESPEC Corp.

(6) Voltage Holding Ratio (VHR)

A horizontal alignment film was formed by applying a horizontal alignment agent to surfaces where ITO patterns of two glass substrates were formed. A spacer was applied on one substrate of the glass substrates such that the horizontal alignment films faced each other and a spacing (cell gap) between the two glass substrates was 4 μm, and, then, the two glass substrates were bound into one element. Then, the liquid crystal composition was injected into this element and enclosed. This element where the liquid crystal was injected was heated at 100 degrees for 24 hours, and irradiated by UV with a wavelength of 365 nm at an energy of 20 J, and, then the voltage holding ratio at 100° C. of this element was measured by using equipment model 6254 manufactured by Toyo Corp. equipped with temperature controller (Model SU-241) equipment manufactured by ESPEC Corp.

Evaluation of Physical Property of the Liquid Crystal Compound Embodiment

Physical properties of the liquid crystal compounds which were synthesized according to the aforementioned Synthesis Examples, respectively, were compared with that of a known material (disclosed in WO1996-011897 and JP1997-176645, M3) and the result is shown in table 3.

TABLE 3

| | Structures | Tc (° C.) | Δn | Δε | γ1 | m.p. (° C.) (rising) | m.p. (° C.) (falling) | Low temp. stability (20 wt %) |
|---|---|---|---|---|---|---|---|---|
| A1 | C₃H₇–[Ph]–[Ph(F,F)]–CF₂O–[Ph(CH₃,F,F,F)]–F | 2 | 0.11 | 20 | 114 | 67 | <30 | 10 days OK |
| A2 | C₃H₇–[Ph]–[Ph(CH₃,F)]–[Ph(F,F)]–CF₂O–[Ph(F,F,F)]–F | 42 | 0.16 | 31 | 285 | 53 | 39 | 10 days OK |
| A3 | C₃H₇–[Ph]–[Ph(F,F)]–[Ph(CH₃,F)]–CF₂O–[Ph(F,F,F)]–F | 107 | 0.21 | 36 | 309 | 70 | <30 | 10 days OK |
| A5 | C₂H₅–[Ph]–[Ph(F,F)]–[Ph(CH₃,F)]–CF₂O–[Ph(F,F,F)]–F | 102 | 0.20 | 33 | 208 | 89 | 74 | 2 days NG |
| A6 | C₂H₅–[THP]–[Ph]–[Ph(CH₃,F)]–CF₂O–[Ph(F,F,F)]–F | 95 | 0.14 | 34 | 269 | 82 | <30 | 2 days NG |
| A7 | C₃H₇–[THP]–[Ph]–[Ph(CH₃,F)]–CF₂O–[Ph(F,F,F)]–F | 114 | 0.16 | 33 | 300 | 66 | <30 | 10 days OK |
| M3 | C₃H₇–[Ph]–[Ph(F,F)]–[Ph(F,F)]–CF₂O–[Ph(F,F,F)]–F | 99 | 0.20 | 31 | 232 | 73 | 58 | 2 days NG |

As may be seen from table 3 and as for the melting point during a temperature fall which affects the low temperature stability, it may be seen that the melting points of A2 and A3 are lower by 20° C. or more than that of the known material M3 which has the same molecular length as the materials according to the present disclosure. It may be seen that the low temperature stability is dramatically improved for A2 and A3 liquid crystals which have the same molecular lengths as M3 which is the conventional liquid crystal.

Also, when a methyl group exists at a specific position as in A3, the dielectric anisotropy is increased by the concentration of about 15% than the M3 liquid crystal. Although A5 among the materials has lower low temperature stability than A1, A2, and A3, it has superior rotational viscosity with respect to dielectric anisotropy than the M3 material which is the conventional material. As shown in the above, the liquid crystal compound has superior low temperature stability and dielectric anisotropy than the conventional liquid crystal, and it is possible to provide a liquid crystal compound which is useful for various devices which use a liquid crystal medium.

Evaluation of Physical Properties of Liquid Crystal Comparative Examples and Embodiments A conventional material M3 compound and the compounds of Formulae 2-4 were mixed by the composition as shown in tables 5-9, and the low temperature stability and the physical property of the liquid crystal composition according to the Comparative Example were evaluated.

The compound of Formula 1 and the compounds of Formulae 2-4 were mixed by the composition as shown in tables 10-39, and the low temperature stability and the physical property of the liquid crystal composition according to an embodiment were evaluated.

Structures for core groups, linkage groups, and terminal groups of the compounds constituting the Comparative Examples 1-5 and the embodiments 1-30 as well as the compounds constituting the Comparative Examples 1-2, and symbols therefor are shown in table 4. In the following embodiments, A1-A7 represent material symbols in the aforementioned Synthesis Examples.

TABLE 4

| structure | symbol |
|---|---|
| Core group | |
| [benzene ring] | A |
| [cyclohexane ring] | B |
| [F-substituted benzene] | C |
| [F-substituted benzene] | D |
| [cyclohexane ring] | B' |
| [diF-substituted benzene] | E |
| [diF-substituted benzene] | F |
| [dioxane ring] | I |

TABLE 4-continued

| structure | symbol |
|---|---|
| [pyran ring] | Ia |
| linkage group | |
| •—CF$_2$O— | X |
| •—CH$_2$CH$_2$— | N |
| •—COO—• | L |
| symbol group | |
| •—C$_n$H$_{2n+1}$ | n (number) |
| •—O—C$_n$H$_{2n+1}$ | On |
| [vinyl] | V |
| [propenyl] | U1 |
| [butenyl] | 3=Z |
| [butenyl] | W |
| [OCF=CF$_2$ group] | OK |
| •—OCF$_3$ | OCF3 |
| •—F | F |
| •—CF$_3$ | CF3 |
| •—CN | CN | separate indications are not provided between core groups and linkage groups core/linkage groups and terminal groups are distinguished by "–".

terminals and terminals are distinguished by ".", and terminals are written for the last time.

For example, notation will be as follows:

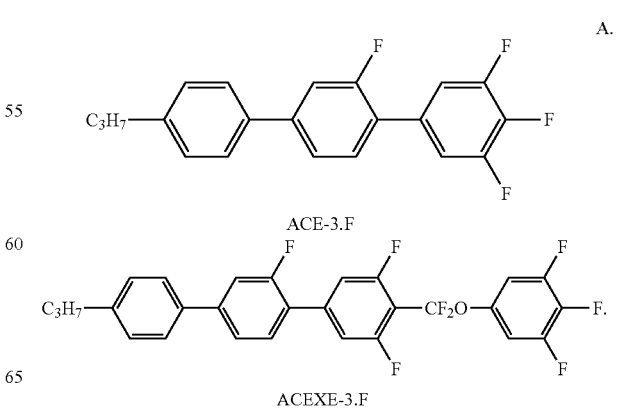

ACE-3.F

ACEXE-3.F

-continued

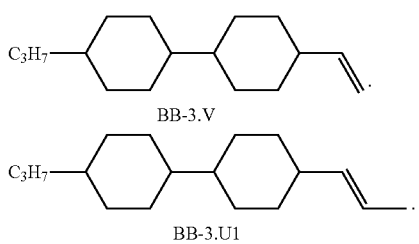

In the following embodiments, when comparing the Comparative Examples 1-2 which used the conventional material M3 with the embodiments 1-2 which used A2 and A3 which were derived from Formula 1, the low temperature stability of the liquid crystal composition of embodiments 1-2 was improved with respect to the Comparative Examples 1-2. Also, it may be seen that the dielectric anisotropy and the rotational viscosity of the liquid crystal composition of embodiments 1-2 may be easily modified.

Also, as for embodiments 3-30, it may be seen that the liquid crystal composition in the embodiments which used the liquid crystal compound derived from Formula 1 has high dielectric anisotropy and various refractive index anisotropy. In particular, since embodiments 10-15 are liquid crystal compositions including the liquid crystal compound of Formula 1 and the liquid crystal compound of Formula 2, embodiments 16-21 are the liquid crystal composition including the liquid crystal compound of Formula 1, the liquid crystal compound of Formula 2, and the liquid crystal compound of Formula 3, and embodiments 22-27 are the liquid crystal compound of Formula 1 and the liquid crystal compound of Formula 4, it may be seen than the liquid crystal composition of various compositions including the liquid crystal compound of Formula 1 exhibits superior properties for a low temperature environment, and that it is possible to form a liquid crystal composition which meet various requirements of the liquid crystal display device.

In addition, embodiments 28-30 is the composition which is formed by additionally mixing the heat/UV stabilizer of Formulae 5-7 to the liquid crystal composition including the liquid crystal compound of Formula 1. In the tables, "additive Formula 5" means a compound of Formula 5 in which $R_1$ is $C_7H_{15}$ and p is 0, and "additive Formula 6" means a compound in which $R_3$ is hydrogen and n is 8. When liquid crystal compositions of Comparative Examples 3-5 are compared with the liquid crystal compositions of embodiments 28-30, it may be seen that the voltage holding ratio of the mixture to which the heat/UV stabilizer was added is at a concentration higher by 10% or more.

Comparative Example 1

TABLE 5

| symbol | content (% by weight) |
| --- | --- |
| BB-3.V | 30.7 |
| BB.3.U1 | 7.9 |
| ACE-2.F | 2.0 |
| ACE-3.F | 6.4 |
| ACE-5.F | 6.8 |
| BAA-5.2 | 3.6 |
| BBE-3.F | 6.0 |
| BBA-3.OCF3 | 3.8 |
| BBCE-3.F | 1.8 |
| ACA-2.3 | 2.2 |

TABLE 5-continued

| symbol | content (% by weight) |
| --- | --- |
| ACA-3.3 | 1.4 |
| BAE-3.F | 4.3 |
| BAA-3.2 | 3.7 |
| BBA-V.1 | 4.4 |
| ACEXE-3.F(M3) | 15 |
| total (wt %) | 100 |

| physical property | low temperature stability (−25° C.) | 15 |
| --- | --- | --- |
| | | NG |
| | Tc | 83.6 |
| | $\Delta n$ | 0.125 |
| | $\Delta \epsilon$ | 8.2 |
| | $\gamma 1$ | 60 |

Comparative Example 2

TABLE 6

| Symbol | content (% by weight) |
| --- | --- |
| BB-3.V | 28.9 |
| BB.3.U1 | 7.4 |
| ACE-2.F | 1.9 |
| ACE-3.F | 6.0 |
| ACE-5.F | 6.4 |
| BAA-5.2 | 3.4 |
| BBE-3.F | 5.6 |
| BBA-3.OCF3 | 3.6 |
| BBCE-3.F | 1.7 |
| ACA-2.3 | 2.1 |
| ACA-3.3 | 1.3 |
| BAE-3.F | 4.0 |
| BAA-3.2 | 3.5 |
| BBA-V.1 | 4.2 |
| ACEXE-3.F(M3) | 20 |
| total (wt %) | 100 |

| physical property | low temperature stability (−25° C.) | 2 days |
| --- | --- | --- |
| | | NG |
| physical property | Tc | 85.3 |
| physical property | $\Delta n$ | 0.131 |
| physical property | $\Delta \epsilon$ | 9.4 |
| physical property | $\gamma 1$ | 65 |

Comparative Example 3

TABLE 7

| Symbol | content (% by weight) |
| --- | --- |
| BB-3.V | 28.0 |
| BAA-3.2 | 3.0 |
| BBA-V.1 | 3.0 |
| BBA-3.1 | 3.0 |
| ACA-3.F | 5.0 |
| BAC-3.F | 10.0 |
| BAE-3.F | 10.0 |
| BBE-3.F | 12.0 |
| A1 | 8.0 |
| A3 | 6.0 |
| A5 | 12.0 |
| total (wt %) | 100.0 |

TABLE 7-continued

| | | |
|---|---|---|
| physical property | low temperature stability (−25° C.) | 20 days OK |
| physical property | $T_c$ | 75.6 |
| physical property | Δn | 0.1207 |
| physical property | Δε | 12.3 |
| physical property | γ1 | 71 |
| physical property | VHR | 72% |

Comparative Example 4

TABLE 8

| Symbol | content (% by weight) |
|---|---|
| BB-3.V | 29.0 |
| BB-3.U | 12.0 |
| BAA-3.2 | 5.0 |
| ACA-3.F | 2.0 |
| BAC-3.F | 13.0 |
| BAE-3.F | 11.0 |
| BBE-3.F | 12.0 |
| A1 | 4.0 |
| A3 | 9.0 |
| A5 | 13.0 |
| total (wt %) | 100.0 |

| | | |
|---|---|---|
| physical property | low temperature stability (−25° C.) | 20 days OK |
| physical property | Tc | 75.3 |
| physical property | Δn | 0.1207 |
| physical property | Δε | 12.4 |
| physical property | γ1 | 76 |
| physical property | VHR | 73% |

Comparative Example 5

TABLE 9

| Symbol | content (% by weight) |
|---|---|
| BB-3.V | 33.0 |
| BAA-3.2 | 3.0 |
| ACA-3.F | 3.0 |
| BAC-3.F | 13.0 |
| BAE-3.F | 13.0 |
| BBE-3.F | 12.0 |
| A3 | 9.0 |
| A5 | 14.0 |
| total (wt %) | 100.0 |

| | | |
|---|---|---|
| physical property | low temperature stability (−25° C.) | 20 days OK |
| physical property | Tc | 75.2 |
| physical property | Δn | 0.1202 |
| physical property | Δε | 12.0 |

TABLE 9-continued

| | | |
|---|---|---|
| physical property | γ1 | 71 |
| physical property | VHR | 75% |

Embodiment 1

TABLE 10

| Symbol | content (% by weight) |
|---|---|
| BB-3.V | 30.7 |
| BB.3.U1 | 7.9 |
| ACE-2.F | 2.0 |
| ACE-3.F | 6.4 |
| ACE-5.F | 6.8 |
| BAA-5.2 | 3.6 |
| BBE-3.F | 6.0 |
| BBA-3.OCF3 | 3.8 |
| BBCE-3.F | 1.8 |
| ACA-2.3 | 2.2 |
| ACA-3.3 | 1.4 |
| BAE-3.F | 4.3 |
| BAA-3.2 | 3.7 |
| BBA-V.1 | 4.4 |
| A2 | 15 |
| total (wt %) | 100 |

| | | |
|---|---|---|
| physical property | low temperature stability (−25° C.) | 20 days OK |
| physical property | Tc | 73.1 |
| physical property | Δn | 0.117 |
| physical property | Δε | 7.4 |
| physical property | γ1 | 62 |

Embodiment 2

TABLE 11

| Symbol | content (% by weight) |
|---|---|
| BB-3.V | 30.7 |
| BB.3.U1 | 7.9 |
| ACE-2.F | 2.0 |
| ACE-3.F | 6.4 |
| ACE-5.F | 6.8 |
| BAA-5.2 | 3.6 |
| BBE-3.F | 6.0 |
| BBA-3.OCF3 | 3.8 |
| BBCE-3.F | 1.8 |
| ACA-2.3 | 2.2 |
| ACA-3.3 | 1.4 |
| BAE-3.F | 4.3 |
| BAA-3.2 | 3.7 |
| BBA-V.1 | 4.4 |
| A3 | 15 |
| total (wt %) | 100 |

| | | |
|---|---|---|
| physical property | low temperature stability (−25° C.) | 20 days OK |
| physical property | Tc | 83.7 |
| physical property | Δn | 0.124 |
| physical property | Δε | 8.3 |

Embodiment 3

TABLE 12

| Symbol | content (% by weight) | |
|---|---|---|
| BB-3.V | 38.4 | |
| BBA-V.1 | 4.4 | |
| BAA-3.2 | 8.2 | |
| BAA-5.2 | 5.5 | |
| BAE-3.F | 6.4 | |
| BBA-3.OCF3 | 6.6 | |
| A1 | 10.6 | |
| A3 | 14.2 | |
| A6 | 3.5 | |
| A7 | 2.2 | |
| total (wt %) | 100.0 | |
| physical property | low temperature stability (−25° C.) | 20 days OK |
| physical property | Tc | 80.3 |
| physical property | $\Delta n$ | 0.1116 |
| physical property | $\Delta \epsilon$ | 10.1 |
| physical property | $\gamma 1$ | 83 |

Embodiment 4

TABLE 13

| Symbol | content (% by weight) | |
|---|---|---|
| BB-3.V | 34.9 | |
| BB-3.U1 | 4.2 | |
| BBA-3.1 | 3.3 | |
| BAA-3.2 | 8.5 | |
| BAA-5.2 | 8.1 | |
| BBA-3.OCF3 | 5.2 | |
| A1 | 16.1 | |
| A3 | 4.5 | |
| A5 | 5.0 | |
| A6 | 7.2 | |
| A7 | 3.0 | |
| total (wt %) | 100.0 | |
| physical property | low temperature stability (−25° C.) | 20 days OK |
| physical property | Tc | 78.8 |
| physical property | $\Delta n$ | 0.1105 |
| physical property | $\Delta \epsilon$ | 10.6 |
| physical property | $\gamma 1$ | 71 |

Embodiment 5

TABLE 14

| Symbol | content (% by weight) | |
|---|---|---|
| BB-3.V | 35.2 | |
| BB-3.U1 | 4.3 | |
| BBA-3.1 | 3.4 | |
| BAA-3.2 | 8.6 | |
| BAA-5.2 | 8.1 | |
| BBA-3.OCF3 | 5.2 | |
| A1 | 15.2 | |
| A3 | 3.0 | |
| A5 | 7.0 | |
| A6 | 10.0 | |
| total (wt %) | 100.0 | |
| physical property | low temperature stability (−25° C.) | 20 days OK |
| physical property | Tc | 78.9 |
| physical property | $\Delta n$ | 0.1105 |
| physical property | $\Delta \epsilon$ | 10.2 |
| physical property | $\gamma 1$ | 70 |

Embodiment 6

TABLE 15

| Symbol | content (% by weight) | |
|---|---|---|
| BB-3.V | 37.7 | |
| BBA-3.1 | 4.5 | |
| BAA-3.2 | 8.6 | |
| BAA-5.2 | 8.6 | |
| BBA-3.OCF3 | 4.7 | |
| A1 | 16.5 | |
| A3 | 3.0 | |
| A5 | 6.4 | |
| A6 | 10.0 | |
| total (wt %) | 100.0 | |
| physical property | low temperature stability (−25° C.) | 20 days OK |
| physical property | Tc | 78.0 |
| physical property | $\Delta n$ | 0.1105 |
| physical property | $\Delta \epsilon$ | 10.0 |
| physical property | $\gamma 1$ | 66 |

Embodiment 7

TABLE 16

| Symbol | content (% by weight) |
|---|---|
| BB-3.V | 39.6 |
| BBA-V.1 | 4.0 |
| BAA-3.2 | 5.5 |

TABLE 16-continued

| | | |
|---|---|---|
| BAA-5.2 | 5.5 | |
| BAE-3.F | 10.0 | |
| BBA-3.OCF3 | 8.0 | |
| A1 | 7.4 | |
| A3 | 8.5 | |
| A5 | 7.0 | |
| A6 | 4.5 | |
| total (wt %) | 100.0 | |
| physical property | low temperature stability (−25° C.) | 20 days OK |
| physical property | Tc | 79.3 |
| physical property | Δn | 0.1099 |
| physical property | Δε | 10.1 |
| physical property | γ1 | 73 |

Embodiment 8

TABLE 17

| Symbol | content (% by weight) | |
|---|---|---|
| BB-3.V | 39.8 | |
| BBA-V.1 | 4.3 | |
| BAA-3.2 | 5.1 | |
| BAA-5.2 | 4.8 | |
| BAE-3.F | 10.8 | |
| BBA-3.OCF3 | 8.6 | |
| A1 | 6.5 | |
| A3 | 7.8 | |
| A5 | 9.1 | |
| A6 | 3.2 | |
| total (wt %) | 100.0 | |
| physical property | low temperature stability (−25° C.) | 20 days OK |
| physical property | Tc | 79.7 |
| physical property | Δn | 0.1098 |
| physical property | Δε | 9.9 |
| physical property | γ1 | 71 |

Embodiment 9

TABLE 18

| Symbol | content (% by weight) | |
|---|---|---|
| BB-3.V | 37.8 | |
| BB-3.U1 | 5.4 | |
| BAA-3.2 | 6.3 | |
| BAA-5.2 | 5.8 | |
| BAE-3.F | 9.7 | |
| BBA-3.OCF3 | 7.8 | |
| A1 | 6.3 | |
| A3 | 7.4 | |
| A5 | 8.7 | |
| A6 | 4.8 | |
| total (wt %) | 100.0 | |

TABLE 18-continued

| | | |
|---|---|---|
| physical property | low temperature stability (−25° C.) | 20 days OK |
| physical property | Tc | 78.8 |
| physical property | Δn | 0.1094 |
| physical property | Δε | 9.9 |
| physical property | γ1 | 70 |

Embodiment 10

TABLE 19

| Symbol | content (% by weight) | |
|---|---|---|
| BB-3.V | 38.1 | |
| BB-3.U1 | 10.0 | |
| BAA-3.2 | 7.5 | |
| BBA-3.1 | 2.6 | |
| ACA-3.F | 6.6 | |
| ACA-5.F | 4.4 | |
| BAE-3.F | 11.4 | |
| BBA-3.OCF3 | 7.0 | |
| A1 | 2.9 | |
| A5 | 9.5 | |
| total (wt %) | 100.0 | |
| physical property | low temperature stability (−25° C.) | 20 days OK |
| physical property | Tc | 78.9 |
| physical property | Δn | 0.1100 |
| physical property | Δε | 6.3 |
| physical property | γ1 | 58 |

Embodiment 11

TABLE 20

| Symbol | content (% by weight) | |
|---|---|---|
| BB-3.V | 37.9 | |
| BB-3.U1 | 10.6 | |
| BAA-3.2 | 6.9 | |
| BBA-3.1 | 3.6 | |
| ACA-3.F | 5.7 | |
| ACA-5.F | 4.4 | |
| BAE-3.F | 11.2 | |
| BBA-3.OCF3 | 7.0 | |
| A1 | 2.3 | |
| A3 | 5.4 | |
| A5 | 5.0 | |
| total (wt %) | 100.0 | |
| physical property | low temperature stability (−25° C.) | 20 days OK |
| physical property | Tc | 80.3 |
| physical property | Δn | 0.1096 |
| physical property | Δε | 6.1 |

TABLE 20-continued

| | | |
|---|---|---|
| property | | |
| physical property | γ1 | 60 |

TABLE 21

Embodiment 12

| Symbol | content (% by weight) |
|---|---|
| BB-3.V | 38.1 |
| BB-3.U1 | 9.5 |
| BAA-3.2 | 5.2 |
| BAA-5.2 | 2.7 |
| BBA-3.1 | 3.2 |
| ACA-3.F | 5.6 |
| ACA-5.F | 4.2 |
| BAE-3.F | 11.4 |
| BBA-3.OCF3 | 7.4 |
| A1 | 2.7 |
| A3 | 10.0 |
| total (wt %) | 100.0 |

| | | |
|---|---|---|
| physical property | low temperature stability (−25° C.) | 20 days OK |
| physical property | Tc | 80.7 |
| physical property | Δn | 0.1095 |
| physical property | Δε | 6.1 |
| physical property | γ1 | 64 |

Embodiment 13

TABLE 22

| Symbol | content (% by weight) |
|---|---|
| BB-3.V | 38.6 |
| BB-3.U1 | 2.8 |
| BAA-3.2 | 8.4 |
| BBA-3.1 | 2.5 |
| ACA-3.F | 6.0 |
| BAC-3.F | 11.3 |
| BAE-3.F | 12.2 |
| BBA-3.OCF3 | 8.5 |
| A1 | 2.6 |
| A3 | 7.1 |
| total (wt %) | 100.0 |

| | | |
|---|---|---|
| physical property | low temperature stability (−25° C.) | 20 days OK |
| physical property | Tc | 80.9 |
| physical property | Δn | 0.1097 |
| physical property | Δε | 6.0 |
| physical property | γ1 | 65 |

Embodiment 14

TABLE 23

| Symbol | content (% by weight) |
|---|---|
| BB-3.V | 36.1 |
| BAA-3.2 | 6.1 |
| BAA-5.2 | 3.5 |
| ACA-3.F | 5.8 |
| BAC-3.F | 11.6 |
| BAE-3.F | 12.6 |
| BBA-3.OCF3 | 14.1 |
| A1 | 5.8 |
| A3 | 4.4 |
| total (wt %) | 100.0 |

| | | |
|---|---|---|
| physical property | low temperature stability (−25° C.) | 20 days OK |
| physical property | Tc | 80.3 |
| physical property | Δn | 0.1105 |
| physical property | Δε | 6.3 |
| physical property | γ1 | 61 |

Embodiment 15

TABLE 24

| Symbol | content (% by weight) |
|---|---|
| BB-3.V | 38.4 |
| BB-3.U1 | 7.2 |
| BAA-3.2 | 6.3 |
| BAA-5.2 | 4.6 |
| ACA-3.F | 6.1 |
| BAE-3.F | 11.0 |
| BBA-3.OCF3 | 9.0 |
| A1 | 4.3 |
| A3 | 5.5 |
| A5 | 7.6 |
| total (wt %) | 100.0 |

| | | |
|---|---|---|
| physical property | low temperature stability (−25° C.) | 20 days OK |
| physical property | Tc | 79.3 |
| physical property | Δn | 0.1105 |
| physical property | Δε | 7.2 |
| physical property | γ1 | 59 |

Embodiment 16

TABLE 25

| symbol | content (% by weight) |
|---|---|
| BB-3.V | 30.0 |
| BBA-V.1 | 5.0 |
| BBA-3.1 | 5.0 |
| ACA-3.F | 8.0 |
| BAE-3.F | 13.0 |

TABLE 25-continued

| | | |
|---|---|---|
| BBE-3.F | 12.0 | |
| A1 | 8.0 | |
| A3 | 7.0 | |
| A5 | 12.0 | |
| total (wt %) | 100.0 | |
| physical property | low temperature stability (−25° C.) | 20 days OK |
| physical property | Tc | 75.6 |
| physical property | Δn | 0.1188 |
| physical property | Δε | 11.5 |
| physical property | γ1 | 74 |
| physical property | | |

Embodiment 17

TABLE 26

| symbol | content (% by weight) |
|---|---|
| BB-3.V | 28.0 |
| BAA-3.2 | 3.0 |
| BBA-V.1 | 3.0 |
| BBA-3.1 | 3.0 |
| ACA-3.F | 5.0 |
| BAC-3.F | 10.0 |
| BAE-3.F | 10.0 |
| BBE-3.F | 12.0 |
| A1 | 8.0 |
| A3 | 6.0 |
| A5 | 12.0 |
| total (wt %) | 100.0 |

| | | |
|---|---|---|
| physical property | low temperature stability (−25° C.) | 20 days OK |
| physical property | Tc | 75.6 |
| physical property | Δn | 0.1207 |
| physical property | Δε | 11.2 |
| physical property | γ1 | 71 |

Embodiment 18

TABLE 27

| symbol | content (% by weight) |
|---|---|
| BB-3.V | 21.0 |
| BB-3.U1 | 4.0 |
| BAA-3.2 | 8.0 |
| ACA-2.F | 5.0 |
| BAE-3.F | 13.0 |
| BBA-3.OCF3 | 9.0 |
| BBE-2.F | 6.0 |
| BBE-3.F | 7.0 |
| A1 | 12.0 |
| A3 | 15.0 |
| total (wt %) | 100.0 |

TABLE 27-continued

| | | |
|---|---|---|
| physical property | low temperature stability (−25° C.) | 20 days OK |
| physical property | Tc | 74.9 |
| physical property | Δn | 0.1194 |
| physical property | Δε | 11.6 |
| physical property | γ1 | 66 |

Embodiment 19

TABLE 28

| symbol | content (% by weight) |
|---|---|
| BB-3.V | 28.0 |
| BAA-3.2 | 3.0 |
| ACA-2.3 | 4.0 |
| ACA-3.3 | 3.0 |
| BAC-3.F | 10.0 |
| BAE-3.F | 12.0 |
| BBA-3.OCF3 | 3.0 |
| BBE-3.F | 10.0 |
| A1 | 9.0 |
| A3 | 9.0 |
| A5 | 9.0 |
| total (wt %) | 100.0 |

| | | |
|---|---|---|
| physical property | low temperature stability (−25° C.) | 20 days OK |
| physical property | Tc | 74.7 |
| physical property | Δn | 0.1260 |
| physical property | Δε | 11.3 |
| physical property | γ1 | 78 |

Embodiment 20

TABLE 29

| symbol | content (% by weight) |
|---|---|
| BB-3.V | 28.0 |
| BAA-3.2 | 3.0 |
| ACA-2.3 | 4.0 |
| ACA-3.3 | 3.0 |
| ACA-3.F | 5.0 |
| BAC-3.F | 5.0 |
| BAE-3.F | 12.0 |
| BBA-3.OCF3 | 3.0 |
| BBE-3.F | 10.0 |
| A1 | 9.0 |
| A3 | 9.0 |
| A5 | 9.0 |
| total (wt %) | 100.0 |

| | | |
|---|---|---|
| physical property | low temperature stability (−25° C.) | 20 days OK |
| physical property | Tc | 75.8 |
| physical property | Δn | 0.1193 |

Embodiment 21

TABLE 30

| symbol | content (% by weight) |
|---|---|
| BB-3.V | 30.0 |
| BAA-5.2 | 5.0 |
| ACA-2.3 | 3.0 |
| ACA-3.3 | 3.0 |
| ACA-3.F | 3.0 |
| BAC-3.F | 10.0 |
| BBA-3.OCF3 | 4.0 |
| BBE-3.F | 10.0 |
| A1 | 12.0 |
| A3 | 11.0 |
| A5 | 9.0 |
| total (wt %) | 100.0 |
| physical property | low temperature stability (−25° C.) 20 days OK |
| physical property | Tc 75.7 |
| physical property | $\Delta n$ 0.1194 |
| physical property | $\Delta \epsilon$ 11.3 |
| physical property | $\gamma 1$ 83 |

Embodiment 22

TABLE 31

| symbol | content (% by weight) |
|---|---|
| BB-3.V | 37.7 |
| BB-3.U1 | 10.0 |
| BAA-3.2 | 3.4 |
| BAA-5.2 | 5.0 |
| ACA-3.F | 6.9 |
| ACA-5.F | 6.9 |
| BAC-3.F | 3.4 |
| BAE-3.F | 8.9 |
| BBA-3.OCF3 | 8.3 |
| BBCE-3.F | 2.0 |
| A1 | 3.4 |
| A5 | 4.1 |
| total (wt %) | 100.0 |
| physical property | low temperature stability (−25° C.) 20 days OK |
| physical property | Tc 81.0 |
| physical property | $\Delta n$ 0.1099 |
| physical property | $\Delta \epsilon$ 5.1 |
| physical property | $\gamma 1$ 59 |

Embodiment 23

TABLE 32

| symbol | content (% by weight) |
|---|---|
| BB-3.V | 37.1 |
| BB-3.U1 | 8.3 |
| BAA-3.2 | 2.7 |
| BAA-5.2 | 6.6 |
| ACA-3.F | 6.7 |
| ACA-5.F | 7.1 |
| BAC-3.F | 5.2 |
| BAE-3.F | 9.2 |
| BBA-3.OCF3 | 6.1 |
| BBCE-3.F | 4.1 |
| A1 | 6.9 |
| total (wt %) | 100.0 |
| physical property | low temperature stability (−25° C.) 20 days OK |
| physical property | Tc 79.8 |
| physical property | $\Delta n$ 0.1105 |
| physical property | $\Delta \epsilon$ 5.1 |
| physical property | $\gamma 1$ 61 |

Embodiment 24

TABLE 33

| symbol | content (% by weight) |
|---|---|
| BB-3.V | 36.5 |
| BB-3.U1 | 10.5 |
| BAA-3.2 | 3.3 |
| BAA-5.2 | 4.9 |
| ACA-3.F | 6.8 |
| ACA-5.F | 6.9 |
| BAC-3.F | 3.3 |
| BAE-3.F | 10.0 |
| BBA-3.OCF3 | 8.5 |
| BBCE-3.F | 2.1 |
| A1 | 3.7 |
| A5 | 3.5 |
| total (wt %) | 100.0 |
| physical property | low temperature stability (−25° C.) 20 days OK |
| physical property | Tc 80.8 |
| physical property | $\Delta n$ 0.1110 |
| physical property | $\Delta \epsilon$ 5.2 |
| physical property | $\gamma 1$ 59 |

Embodiment 25

TABLE 34

| symbol | content (% by weight) |
|---|---|
| BB-3.V | 38.6 |
| BB-3.U1 | 11.0 |

TABLE 34-continued

| | | |
|---|---|---|
| BAA-5.2 | 5.4 | |
| ACA-3.F | 7.7 | |
| ACA-5.F | 7.7 | |
| BAC-3.F | 3.3 | |
| BAE-3.F | 10.7 | |
| BBA-3.OCF3 | 7.5 | |
| BBCE-3.F | 2.1 | |
| A1 | 2.5 | |
| A5 | 3.5 | |
| total (wt %) | 100.0 | |
| physical property | low temperature stability (−25° C.) | 20 days OK |
| physical property | Tc | 77.3 |
| physical property | Δn | 0.1088 |
| physical property | Δε | 4.9 |
| physical property | γ1 | 53 |

Embodiment 26

TABLE 35

| symbol | content (% by weight) |
|---|---|
| BB-3.V | 38.4 |
| BB-3.U1 | 10.1 |
| BAA-3.2 | 3.5 |
| BAA-5.2 | 5.0 |
| ACA-2.F | 2.4 |
| ACA-3.F | 5.3 |
| ACA-5.F | 5.3 |
| BAC-3.F | 3.3 |
| BAE-3.F | 11.2 |
| BBA-3.OCF3 | 6.5 |
| BBCE-3.F | 2.1 |
| A1 | 3.7 |
| A5 | 3.2 |
| total (wt %) | 100.0 |

| | | |
|---|---|---|
| physical property | low temperature stability (−25° C.) | 20 days OK |
| physical property | Tc | 77.2 |
| physical property | Δn | 0.1087 |
| physical property | Δε | 5.0 |
| physical property | γ1 | 54 |

Embodiment 27

TABLE 36

| symbol | content (% by weight) |
|---|---|
| BB-3.V | 38.7 |
| BB-3.U1 | 5.0 |
| BB-3.4 | 6.1 |
| BAA-3.2 | 4.5 |
| BAA-5.2 | 3.9 |
| BBA-3.1 | 1.0 |
| ACA-3.F | 7.6 |
| ACA-5.F | 7.4 |

TABLE 36-continued

| | | |
|---|---|---|
| BAE-3.F | 10.0 | |
| BBA-3.OCF3 | 5.5 | |
| BBCE-3.F | 2.0 | |
| A1 | 3.1 | |
| A3 | 5.2 | |
| total (wt %) | 100.0 | |
| physical property | low temperature stability (−25° C.) | 20 days OK |
| physical property | Tc | 79.3 |
| physical property | Δn | 0.1095 |
| physical property | Δε | 5.1 |
| physical property | γ1 | 56 |

Embodiment 28

TABLE 37

| symbol | content (% by weight) |
|---|---|
| BB-3.V | 28.0 |
| BAA-3.2 | 3.0 |
| BBA-V.1 | 3.0 |
| BBA-3.1 | 3.0 |
| ACA-3.F | 5.0 |
| BAC-3.F | 10.0 |
| BAE-3.F | 10.0 |
| BBE-3.F | 12.0 |
| A1 | 8.0 |
| A3 | 6.0 |
| A5 | 12.0 |
| total (wt %) | 100.0 |
| additive Formula 5 | 0.03 |
| additive Formula 6 | 0.03 |

| | | |
|---|---|---|
| physical property | low temperature stability (−25° C.) | 20 days OK |
| physical property | Tc | 75.6 |
| physical property | Δn | 0.1207 |
| physical property | Δε | 12.3 |
| physical property | γ1 | 71 |
| physical property | VHR | 82% |

Embodiment 29

TABLE 38

| symbol | content (% by weight) |
|---|---|
| BB-3.V | 29.0 |
| BB-3.U1 | 2.0 |
| BAA-3.2 | 5.0 |
| ACA-3.F | 2.0 |
| BAC-3.F | 13.0 |
| BAE-3.F | 11.0 |
| BBE-3.F | 12.0 |
| A1 | 4.0 |
| A3 | 9.0 |
| A5 | 13.0 |
| total (wt %) | 100.0 |
| additive Formula 5 | 0.03 |
| additive Formula 6 | 0.03 |

TABLE 38-continued

| physical property | low temperature stability (−25° C.) | 20 days OK |
|---|---|---|
| physical property | Tc | 75.3 |
| physical property | Δn | 0.1207 |
| physical property | Δε | 12.4 |
| physical property | γ1 | 76 |
| physical property | VHR | 85% |

Embodiment 30

TABLE 39

| symbol | content (% by weight) |
|---|---|
| BB-3.V | 33.0 |
| BAA-3.2 | 3.0 |
| ACA-3.F | 3.0 |
| BAC-3.F | 13.0 |
| BAE-3.F | 13.0 |
| BBE-3.F | 12.0 |
| A3 | 9.0 |
| A5 | 14.0 |
| total (wt %) | 100.0 |
| additive Formula 5 | 0.03 |
| additive Formula 6 | 0.03 |
| physical property | low temperature stability (−25° C.) | 20 days OK |
| physical property | Tc | 75.2 |
| physical property | Δn | 0.1202 |
| physical property | Δε | 12.0 |
| physical property | γ1 | 71 |
| physical property | VHR | 84% |

While the present disclosure has been particularly shown and described with reference to exemplary embodiments thereof, it will be understood by those of ordinary skill in the art that various changes in form and details may be made therein without departing from the spirit and scope of the present disclosure as defined by the following claims.

What is claimed is:

1. A liquid crystal display device comprising:
   a first substrate;
   a second substrate facing the first substrate;
   an electrode part provided on at least one of the first substrate and the second substrate; and
   a liquid crystal layer provided between the first substrate and the second substrate, the liquid crystal layer comprising a liquid crystal composition,
   wherein the liquid crystal composition comprises at least one liquid crystal compound represented as Formula 1 and at least one liquid crystal compound represented as Formula 2,

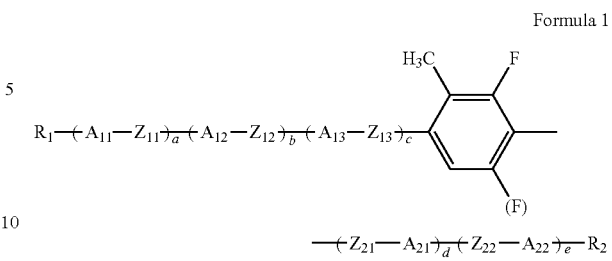

Formula 1 wherein $R_1$ is hydrogen or an alkyl having 1-15 carbon atoms, in which at least one —$CH_2$— group may be independently replaced by —C≡C—, —$CF_2$O—, —CH=CH—, —O—, —CO—O—, —O—CO— or —O—CO—O— in such a way that no two oxygen atoms bind to each other, and one to three hydrogen atoms may be replaced by halogen atoms, wherein $R_2$ is —F, —Cl, —$CF_3$, —$CHF_2$, —$CH_2F$, —$OCF_3$, —CN, —NCS, or an alkyl having 1-5 carbon atoms substituted with one to three of —F, and —$CH_2$— groups are optionally replaced by O atoms independently of each other, in such a way that no two oxygen atoms bind each other, wherein (F) represents that a hydrogen atom is optionally replaced by —F, wherein $A_{11}$, $A_{12}$, $A_{13}$, $A_{21}$ and $A_{22}$, represent one of the following structures independently of each other:

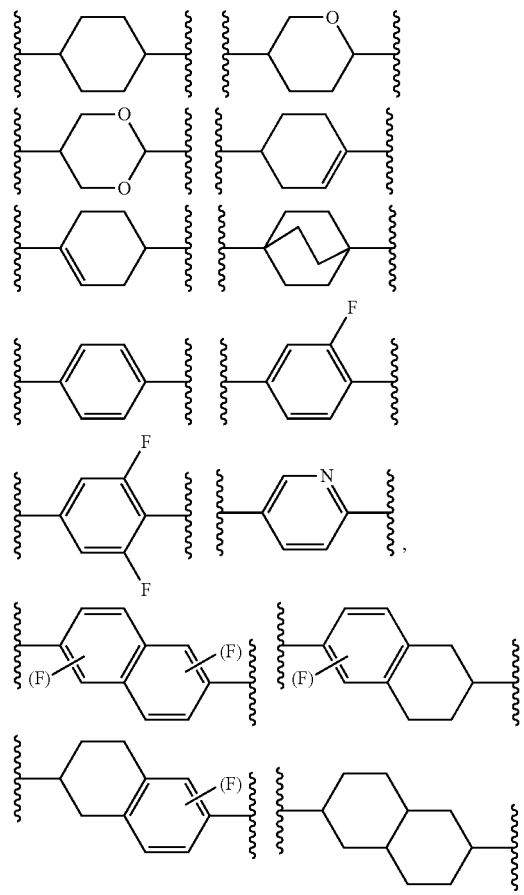

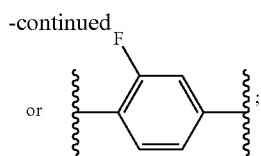

and wherein $Z_{11}$, $Z_{12}$, $Z_{13}$, $Z_{21}$ and $Z_{22}$, are each independently a single bond, —CH$_2$CH$_2$—, —CH=CH—, —CH$_2$O—, —OCH$_2$—, —C≡C—, —CH$_2$CF$_2$—, —CHFCHF—, —CF$_2$CH$_2$—, —CH$_2$CHF—, —CHFCH$_2$—, —C$_2$F$_4$—, —COO—, —OCO—, —CF$_2$O—, or —OCF$_2$— independently of each other; and a, b, c, d and e, are each independently an integer from 0 to 3, and a+b+c+d+e is less than or equal to 5, Formula 2

wherein $R_{11}$ is the same as in the definition for $R_1$ in Formula 1, $R_{21}$, in addition to the definition of $R_1$ in Formula 1, represents —F, —Cl, —CF$_3$, or —OCF$_3$, $A_3$ and $A_4$ are 1,4-cyclohexylene or 1,4-phenylene, independently, and $A_5$ represents one of the following structures:

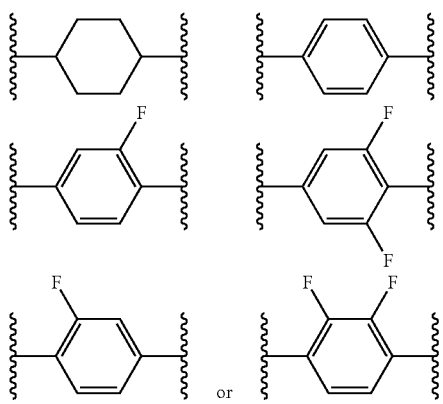

2. A liquid crystal composition comprising at least one liquid crystal compound represented as Formula 1 and at least one liquid crystal compound represented by Formula 2, wherein, $R_1$ is hydrogen or an alkyl having 1-15 carbon atoms, in which at least one —CH$_2$— group may be independently replaced by —C≡C—, —CF$_2$O—, —CH=CH—, —O—, —CO—O—, —O—CO— or —O—CO—O— in such a way that no two oxygen atoms bind to each other, and one to three hydrogen atoms may be replaced by halogen atoms, wherein $R_2$ is —F, —Cl, —CF$_3$, —CHF$_2$, —CH$_2$F, —OCF$_3$, —CN, —NCS, or an alkyl having 1-5 carbon atoms substituted with one to three of —F, and —CH$_2$— groups are optionally replaced by O atoms independently of each other, in such a way that no two oxygen atoms bind each other, wherein (F) represents that a hydrogen atom is optionally replaced by —F, wherein $A_{11}$, $A_{12}$, $A_{13}$, $A_{21}$ and $A_{22}$, represent one of the following structures independently of each other:

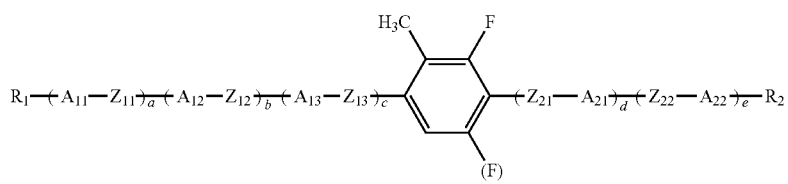

Formula 1

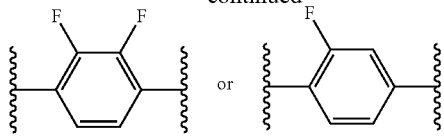

and wherein $Z_{11}$, $Z_{12}$, $Z_{13}$, $Z_{21}$ and $Z_{22}$, are each independently a single bond, —CH$_2$CH$_2$—, —CH=CH—, —CH$_2$O—, —OCH$_2$—, —C≡C—, —CH$_2$CF$_2$—, —CHFCHF—, —CF$_2$CH$_2$—, —CH$_2$CHF—, —CHFCH$_2$—, —C$_2$F$_4$—, —COO—, —OCO—, —CF$_2$O—, or —OCF$_2$—;

a, b, c, d and e, are each independently an integer from 0 to 3, and a+b+c+d+e is less than or equal to 5, Formula 2

wherein $R_{11}$ is the same as in the definition for $R_1$ in Formula 1, $R_{21}$, in addition to the definition of $R_1$ in Formula 1, represents —F, —Cl, —CF$_3$, or —OCF$_3$, $A_3$ and $A_4$ are 1,4-cyclohexylene or 1,4-phenylene, independently, and $A_5$ represents one of the following structures:

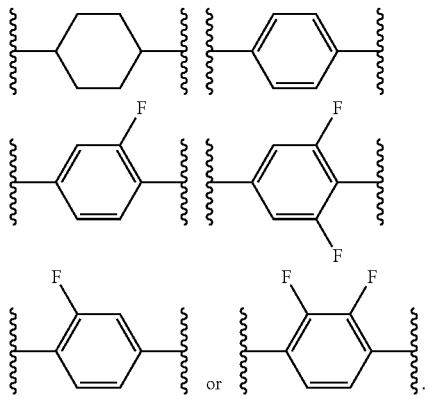

3. The liquid crystal composition according to claim 2, wherein at least one of $Z_{11}$, $Z_{12}$, $Z_{13}$, $Z_{21}$ and $Z_{22}$ is —CF$_2$O—.

4. The liquid crystal composition according to claim 2, wherein d and e are 0, and $R_2$ is —F, —OCF$_3$ or —CF$_3$.

5. The liquid crystal composition according to claim 2, further comprising a liquid crystal compound represented as Formula 2-1 or Formula 2-2, Formula 2-1

Formula 2-2

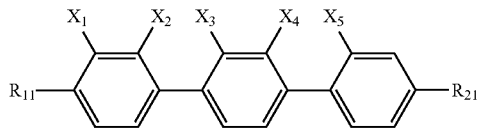

wherein $R_{11}$, $R_{21}$ and $A_5$ are independently the same as in the definitions for Formula 2, $X_1$ to $X_5$, are —H or —F independently, and at least one of $X_3$ and $X_4$ is —F.

6. The liquid crystal composition according to claim 2, further comprising a liquid crystal compound represented as Formula 3

Formula 3

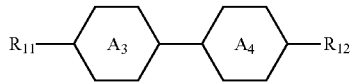

wherein $R_{11}$ and $R_{12}$ are independently the same as in the definition of $R_1$ in Formula 1, and $A_3$ and $A_4$ are independently 1,4-cyclohexylene or 1,4-phenylene.

7. The liquid crystal composition according to claim 6, wherein the liquid crystal compound represented as Formula 3 is represented as Formula 3-1 or Formula 3-2, Formula 3-1

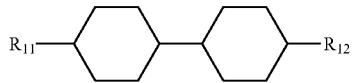

Formula 3-2

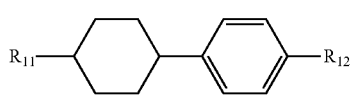

wherein $R_{11}$ and $R_{12}$ are independently the same as in the definition of $R_1$ in Formula 1.

8. The liquid crystal composition according to claim 2, further comprising a liquid crystal compound represented as Formula 4

Formula 4

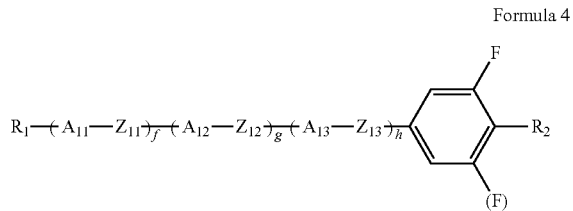

wherein $R_1$ and $R_2$ are the same as in the definitions of $R_1$ and $R_2$ in Formula 1, $A_{11}$, $A_{12}$, $A_{13}$, $Z_{11}$, $Z_{12}$ and $Z_{13}$ are also the same as in the definitions of $A_{11}$, $A_{12}$, $A_{13}$, $Z_{11}$, $Z_{12}$, and $Z_{13}$ in Formula 1, f, g, and h are each independently an integer of 0 or 1, and f+g+h is 2 or 3.

9. The liquid crystal composition according to claim 2, further comprising a pitch modifying agent represented as Formula 8, Formula 8

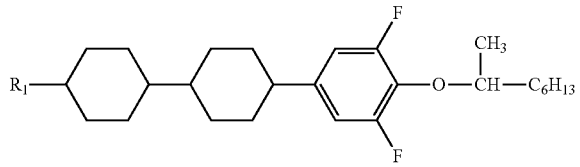

wherein R₁ is the same in the definition for Formula 1.

10. The liquid crystal composition according to claim 2, wherein the liquid crystal compound of Formula 1 is represented as Formula 1-2, Formula 1-2

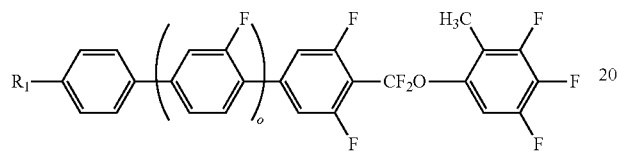

and the liquid crystal composition further comprises a liquid crystal compound represented as 3-1-1 and a compound represented as Formula 5

Formula 3-1-1

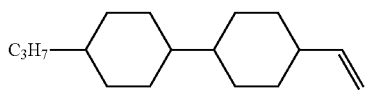

Formula 5

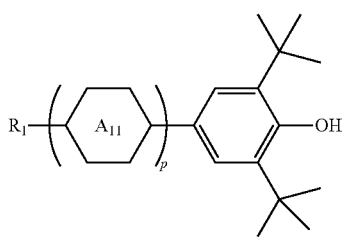

wherein o is an integer of 0 or 1, R₁ and A₁₁ are the same as in the definitions for Formula 1, p is an integer of 0 or 1.

11. The liquid crystal composition according to claim 10, wherein the liquid crystal composition comprises 3-35 parts by weight of the liquid crystal compound represented as Formula 1-2, 15-45 parts by weight of the liquid crystal compound represented as Formula 3-1-1, and 0.01-0.05 parts by weight of the liquid crystal compound represented as Formula 5.

12. The liquid crystal composition according to claim 2, wherein the liquid crystal composition of Formula 1 comprises a liquid crystal compound represented as Formula 1-2-2 and a liquid crystal compound represented as Formula 1-2-3

Formula 1-2-2

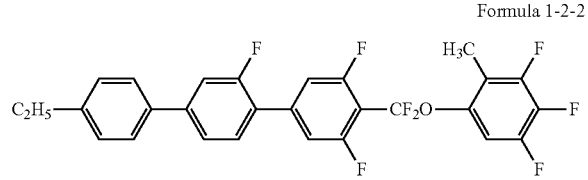

-continued

Formula 1-2-3

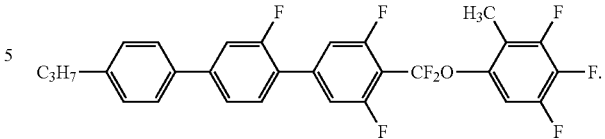

13. The liquid crystal composition according to claim 12, wherein a weight ratio between the liquid crystal compound of Formula 1-2-2 and the liquid crystal compound of Formula 1-2-3 is 1:0.5-1:2.0.

14. The liquid crystal composition according to claim 2, wherein the liquid crystal compound of Formula 1 is represented as Formula 1-2, Formula 1-2

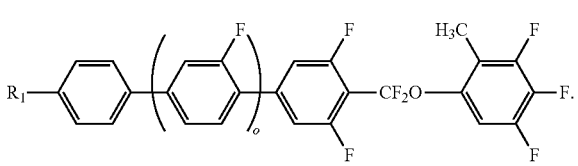

wherein R₁ is the same as in the definition for Formula 1, o is an integer of 0 or 1, and wherein the liquid crystal composition further comprises at least one liquid crystal compound represented as Formula 2-1-1-1, a liquid crystal compound represented as Formula 2-1-1-2, and a liquid crystal compound represented as Formula 4-1-1-1, Formula 2-1-1

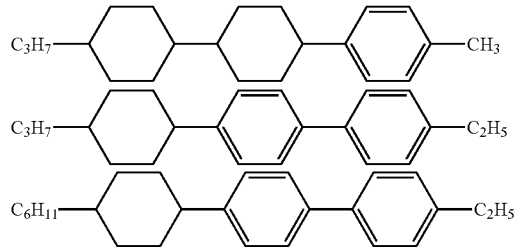

Formula 2-1-1-2

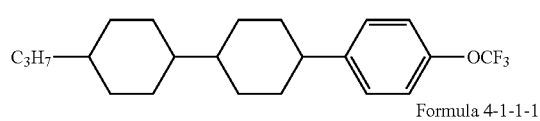

Formula 4-1-1-1

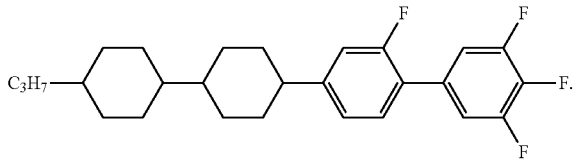

15. The liquid crystal composition according to claim 14, wherein the liquid crystal composition comprises 5-20 parts by weight of at least one of the liquid crystal compounds represented as Formula 1-2 and the liquid crystal compound represented as Formula 2-1-1-1, 5-20 parts by weight of the liquid crystal compound represented as Formula 2-1-1-2, and 2-10 parts by weight of the liquid crystal compound represented as Formula 4-1-1-1.

16. The liquid crystal composition according to claim 2, wherein the liquid crystal compound of Formula 1 is represented as Formula 1-2, Formula 1-2

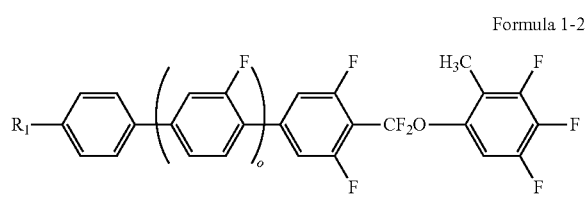

wherein the liquid crystal composition further comprises a liquid crystal compound represented as Formula 3-1-1, a liquid crystal compound represented as Formula 2-2-1-1, and a liquid crystal compound represented as Formula 4-1-2

Formula 3-1-1

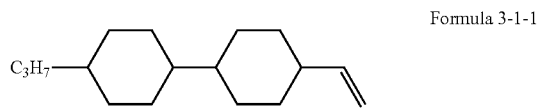

Formula 2-2-1-1

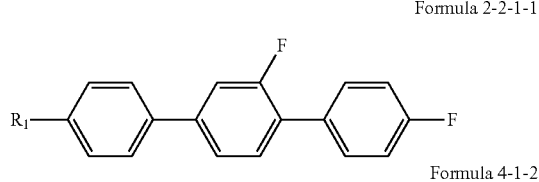

Formula 4-1-2

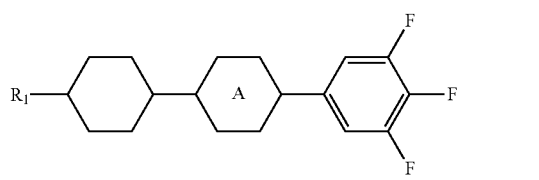

wherein A represents one of following structures:

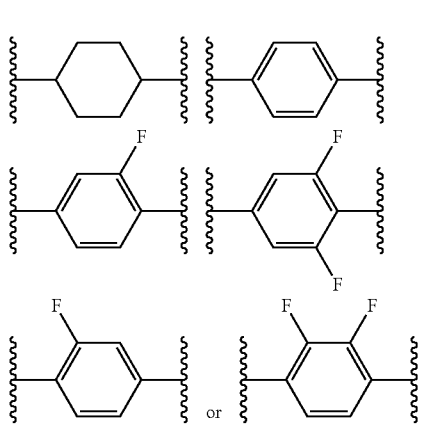

and wherein $R_1$ is the same as in the definition for Formula 1, and o is an integer of 0 or 1.

17. The liquid crystal composition according to claim 16, wherein the liquid crystal composition comprises 15-45 parts by weight of the liquid crystal compound represented as Formula 3-1-1, 2-15 parts by weight of the liquid crystal compound represented as Formula 2-2-1-1, and 3-35 parts by weight of the liquid crystal compound represented as Formula 4-1-2.

18. The liquid crystal composition according to claim 2, wherein the liquid crystal compound of Formula 1 is one of the compounds represented as the following structures:

[1]
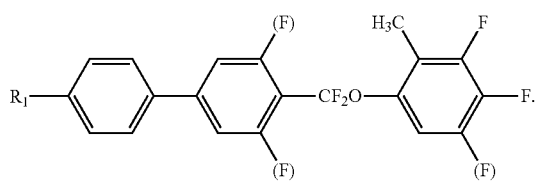

[2]
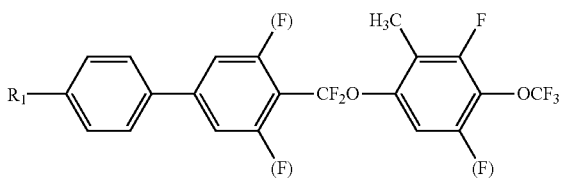

[3]
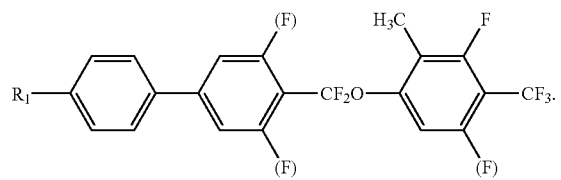

[4]
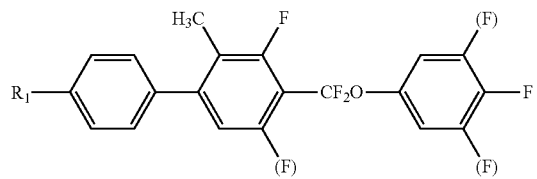

[5]
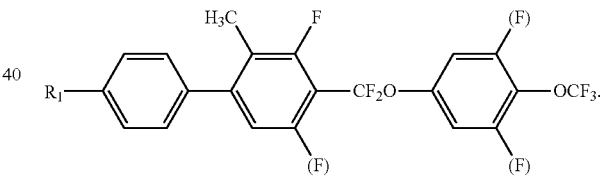

[6]
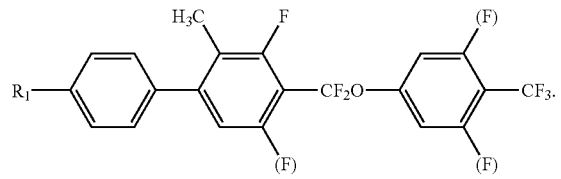

[7]
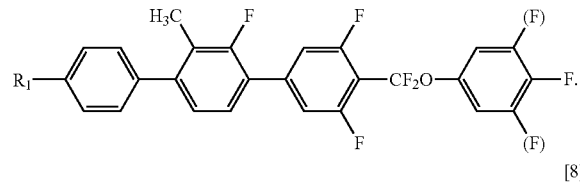

[8]
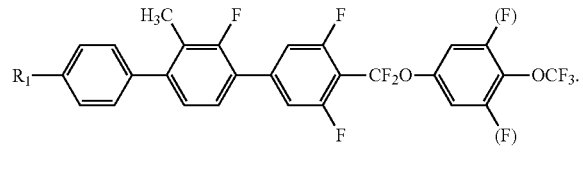

-continued
[9]
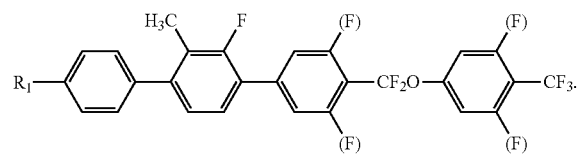
[10]
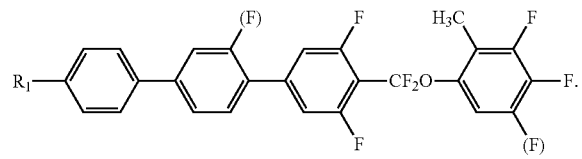
[11]
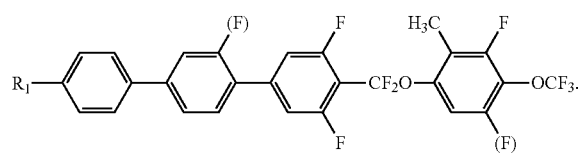
[12]
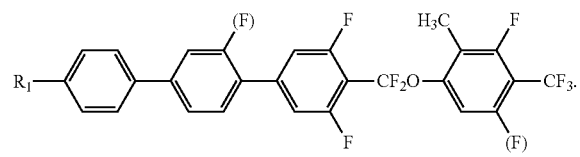
[13]
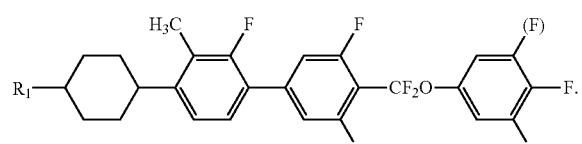
[14]
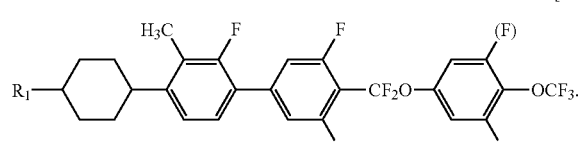
[15]
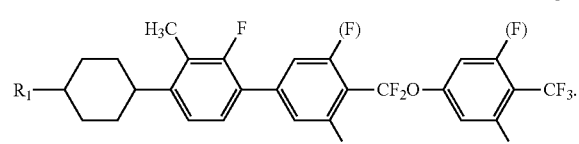
[16]
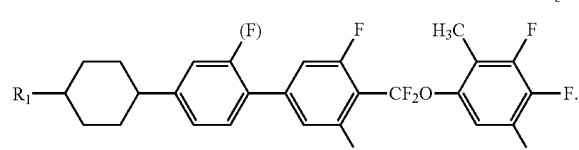
[17]
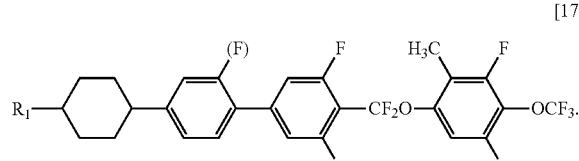
-continued
[18]
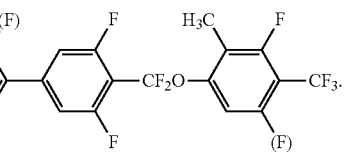
[19]
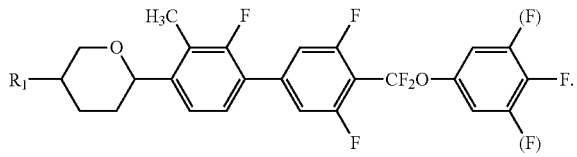
[20]
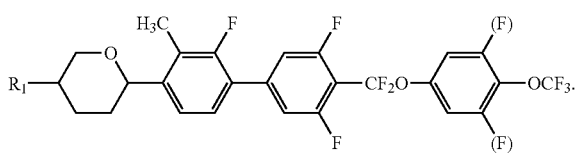
[21]
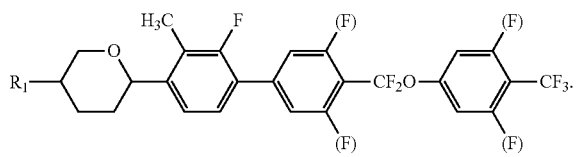
[22]
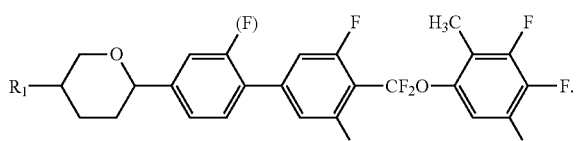
[23]
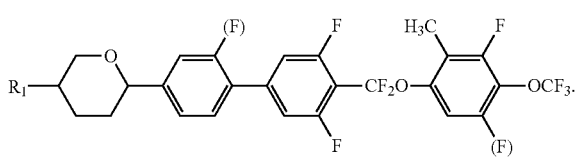
[24]
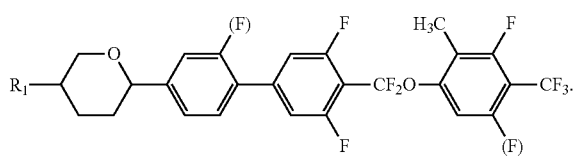
[25]
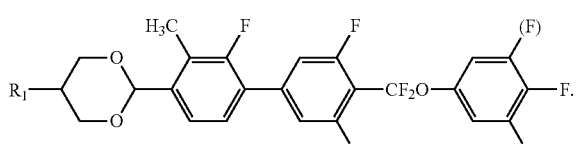
[26]
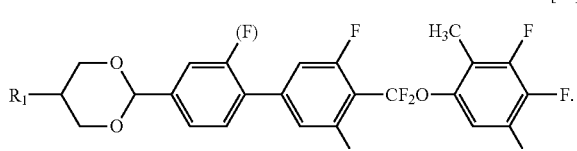

-continued

[27]
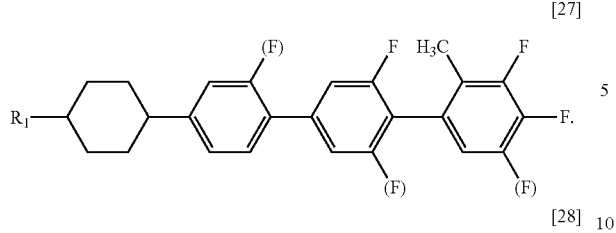

[28]
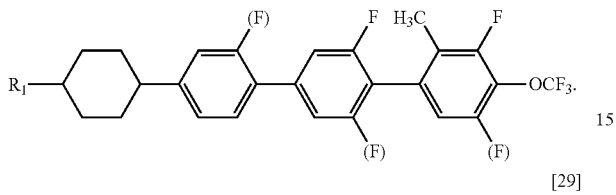

[29]
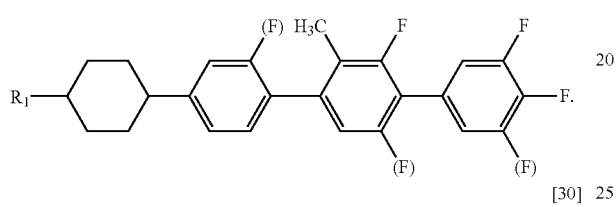

[30]
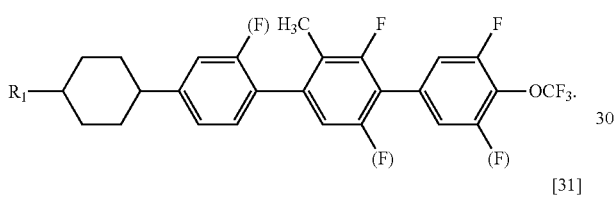

[31]
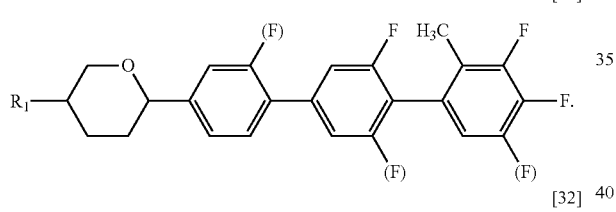

[32]
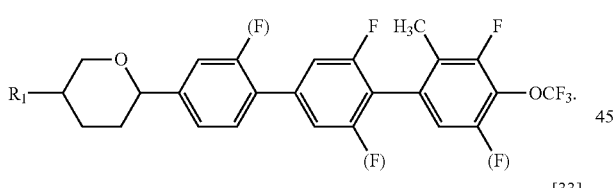

[33]
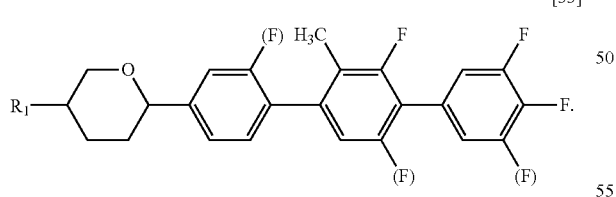

[34]
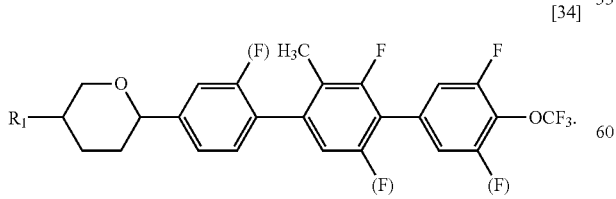

19. A liquid crystal composition comprising at least one liquid crystal compound represented as Formula 1 and at least one, compound represented as Formulae 5-7, Formula 1
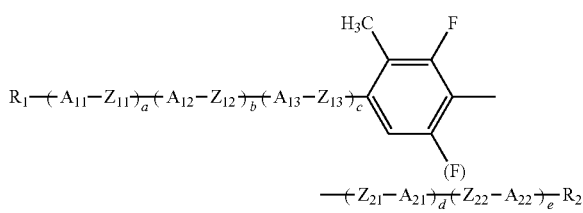

wherein $R_1$ is hydrogen or an alkyl having 1-15 carbon atoms, in which at least one —$CH_2$— group may be independently replaced by —C≡C—, —$CF_2O$—, —CH=CH—, —O—, —CO—O—, —O—CO— or —O—CO—O— in such a way that no two oxygen atoms bind to each other, and one to three hydrogen atoms may be replaced by halogen atoms, wherein $R_2$ is —F, —Cl, —$CF_3$, —$CHF_2$, —$CH_2F$, —$OCF_3$, —CN, —NCS, or an alkyl having 1-5 carbon atoms substituted with one to three of —F, and —$CH_2$— groups are optionally replaced by O atoms independently of each other, in such a way that no two oxygen atoms bind each other, wherein (F) represents that a hydrogen atom is optionally replaced by —F, wherein $A_{11}$, $A_{12}$, $A_{13}$, $A_{21}$ and $A_{22}$, represent one of the following structures independently of each other:

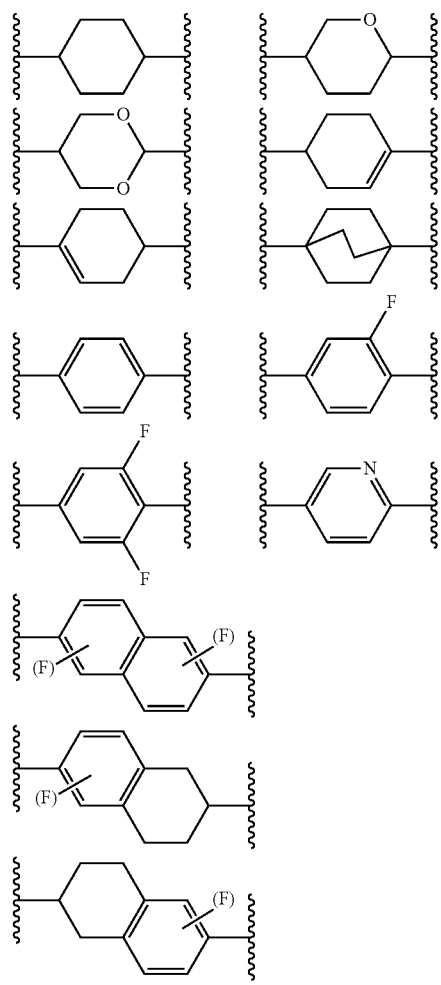

-continued

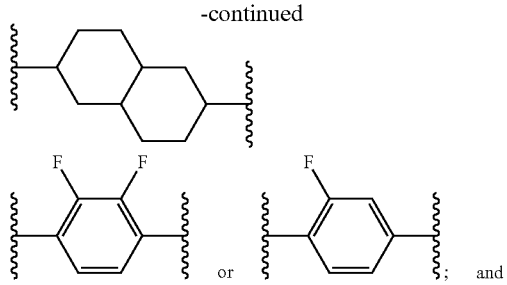

or ; and and wherein $Z_{11}$, $Z_{12}$, $Z_{13}$, $Z_{21}$ and $Z_{22}$, are each independently a single bond, —$CH_2CH_2$—, —CH=CH—, —$CH_2O$—, —$OCH_2$—, —C≡C—, —$CH_2CF_2$—, —CHFCHF—, —$CF_2CH_2$—, —$CH_2CHF$—, —$CHFCH_2$—, —$C_2F_4$—, —COO—, —OCO—, —$CF_2O$—, or —$OCF_2$— independently of each other; and a, b, c, d and e, are each independently an integer from 0 to 3, and a+b+c+d+e is less than or equal to 5, Formula 5

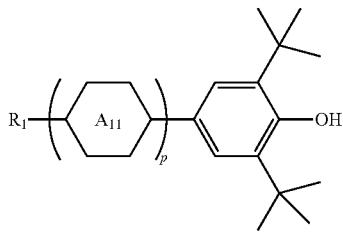

-continued

Formula 6

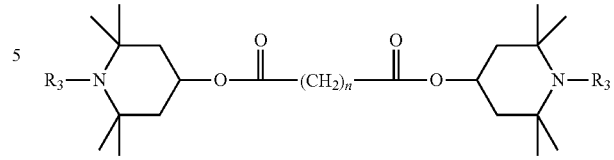

Formula 7

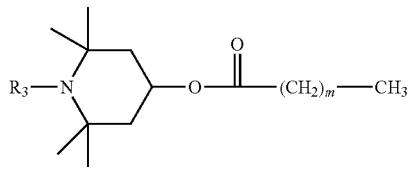

wherein $R_1$, $A_{11}$ are the same as in the definitions for Formula 1, p is an integer of 0 or 1, $R_3$ represents hydrogen, oxygen radical, or an alkyl having 1-15 carbon atoms, in which at least one —$CH_2$-group may be independently replaced by —C≡C—, —$CF_2O$—, —CH=CH—, —O—, —CO—O—, —O—CO— or —O—CO—O— in such a way that no two oxygen atoms bind to each other, one to three hydrogen atoms may be replaced by halogen atoms, n is an integer of 1-12, and m is an integer of 0-12.

* * * * *